(12) United States Patent
Auchinleck

(10) Patent No.: US 8,261,981 B2
(45) Date of Patent: Sep. 11, 2012

(54) APPARATUS AND METHODS FOR MONITORING TRANSFUSION OF BLOOD

(75) Inventor: Geoffrey Fletcher Auchinleck, Vancouver (CA)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 12/354,120

(22) Filed: Jan. 15, 2009

(65) Prior Publication Data

US 2009/0121009 A1 May 14, 2009

Related U.S. Application Data

(63) Continuation of application No. 11/061,899, filed on Feb. 18, 2005, now Pat. No. 7,490,766, which is a continuation-in-part of application No. 10/783,438, filed on Feb. 19, 2004, now Pat. No. 6,983,884.

(51) Int. Cl.
*G07B 15/02* (2011.01)
(52) U.S. Cl. ............... 235/384; 235/385; 235/462.07; 700/86; 700/242; 705/2; 238/117; 604/67

(58) Field of Classification Search ............... 235/384, 235/385, 462.07; 700/86, 242; 705/2; 238/117; 604/67
See application file for complete search history.

(56) References Cited

U.S. PATENT DOCUMENTS

| | | | |
|---|---|---|---|
| 4,953,745 A | | 9/1990 | Rowlett, Jr. |
| 5,193,855 A | * | 3/1993 | Shamos ................. 283/117 |
| 5,790,409 A | | 8/1998 | Fedor et al. |
| 5,912,818 A | | 6/1999 | McGrady et al. |
| 6,260,761 B1 | * | 7/2001 | Peoples, Jr. ............ 235/462.07 |
| 7,349,858 B1 | | 3/2008 | McGrady et al. |
| 2002/0068358 A1 | * | 6/2002 | Campbell et al. ......... 435/289.1 |
| 2004/0186376 A1 | * | 9/2004 | Hogg et al. ............... 600/424 |
| 2005/0119914 A1 | * | 6/2005 | Batch ....................... 705/2 |
| 2008/0103437 A1 | * | 5/2008 | Duchon et al. ............ 604/67 |
| 2009/0204508 A1 | * | 8/2009 | Podgurny et al. .......... 705/26 |

* cited by examiner

*Primary Examiner* — Allyson Trail

(57) ABSTRACT

Apparatus and methods are described for ensuring that blood transfused into a patient is the correct blood for that patient, is transfused in the correct manner and that a complete audit trail is created that will allow later tracing of blood from donation through to ultimate transfusion.

20 Claims, 13 Drawing Sheets

*Alternate embodiment of battery architecture to achieve parallel, and if needed, independent charging of serially connected battery cells.*

*Alternate embodiment of battery architecture to achieve parallel, and if needed, independent charging of serially connected battery cells.*

*Preferred embodiment of battery architecture to achieve parallel, and if needed, independent charging of serially connected battery cells.*

Preferred embodiment of serially connected battery with parallel charging ability with sensors.

*Serially connected battery architecture with chargers.*

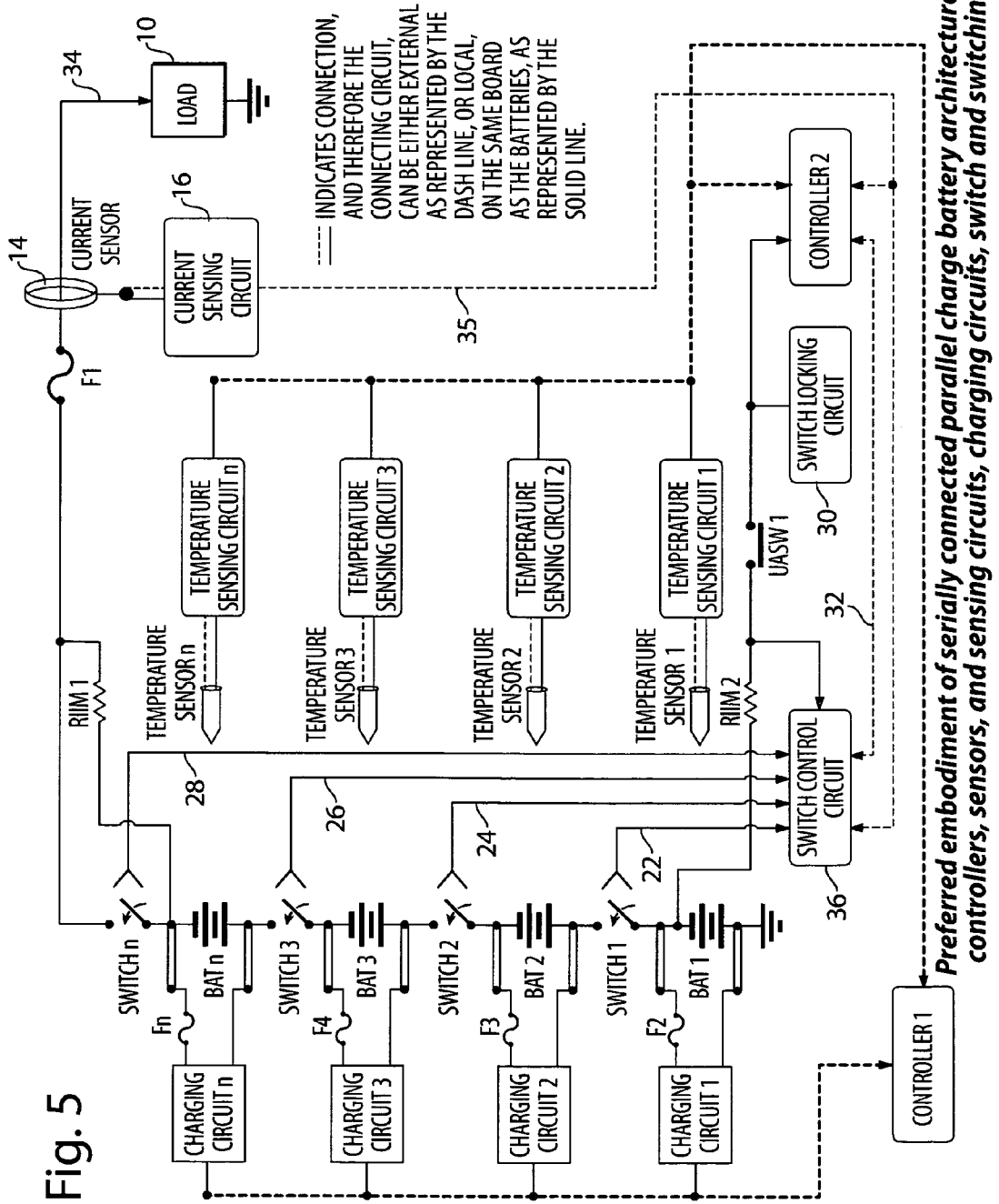

APPARATUS AND METHODS FOR MONITORING TRANSFUSION OF BLOOD

CROSS REFERENCE TO RELATED APPLICATIONS

This application is a continuation of and claims priority to U.S. patent application Ser. No. 11/061,899 filed Feb. 18, 2005, which is a continuation-in-part of and claims priority to U.S. patent application Ser. No. 10/783,438 filed Feb. 19, 2004, now U.S. Pat. No. 6,983,884, issued Jan. 10, 2006, which applications and patents are incorporated by reference herein in their entirety.

BACKGROUND OF THE INVENTION

1. Technical Field of the Invention

The present invention relates generally to apparatus and methods for monitoring the handling, transportation, and transfusion of blood and/or blood products. Apparatus and methods presented herein employ electronically readable indicia to confirm the identity of patients, blood units, and caregivers every time a blood unit is handled. The present invention further relates to the collection, storage, and communication of information relevant to transfusions such that complete audit trails are recorded and guidance to the caregiver is provided in order to ensure that all required procedures are executed properly.

2. Description of the Related Art

Transfusion of blood is a high-risk procedure. A patient may be killed or seriously harmed if the wrong type of blood or blood product is transfused, may be infected by blood bourn pathogens or may have unexpected reactions to blood products. For these reasons, considerable care is taken in the collection, processing, packaging, labeling and transport of blood units. Blood collection and supply agencies (Canadian Blood Services (Canada), American Red Cross, America's Blood Centers (USA), National Blood Services (UK)) keep detailed records of donations, processing, packaging and transport of blood products so that any single blood product can be traced back to an individual donor. Using this information, it should be possible to find and inform all patients who may have been exposed to blood from a particular donor that they might be at risk should a problem arise.

Blood transfusions are usually performed at hospitals. Hospital blood banks receive blood from the blood supply agency, perform any tests they may require to assure the type and quality of the blood and place the blood into the blood bank stock.

The first step in the transfusion process is testing of the patient's blood. This requires that a blood sample be drawn from the patient, correctly labeled with the patient's identification, and sent to the blood laboratory. The laboratory tests the patient's blood to determine the correct blood type for the patient, and any special requirements the patient may have. Once these factors are known, a suitable blood unit is retrieved from the blood bank stock and is labeled as suitable for the particular patient. The designated blood unit is placed into a storage location until it is needed. The blood laboratory keeps detailed records of the testing of the blood unit and the patient's blood.

The detailed records of the patient's blood test results, blood type and requirements is usually stored in a blood bank computer system (McKesson Corporation, www.mckesson.com, Misys, www.misys.com, Meditech, www.meditech.com and many others). This information, along with a history of previous blood transfusions, may be used to quickly allocate additional blood units for the patient without the need to repeat the original blood test, in a process call 'electronic issue' of blood units.

When the patient requires blood for transfusion, someone is sent to the blood bank to collect the prepared blood unit. They are expected to ensure that they have collected the correct blood unit, and to record the time that the blood unit was retrieved. Accepted practice requires that blood that has remained outside of refrigeration for more than 30 minutes should not be transfused. It is the responsibility of the person collecting the blood from the blood bank to ensure that it is promptly delivered.

The transfusion step is tightly controlled. The caregiver administering the blood is required to follow a strict procedure that includes careful checking to ensure that the blood is labeled for the patient to be transfused, that the label is on the right blood unit, and that the unit is the correct blood type, meets any special requirements for the patient and has not expired. All of these checks are recorded to ensure that a full audit trail exists for the transfusion event, and to confirm that the correct checks were performed. This audit trail is the only means to link the original blood donation to the patient.

During the transfusion process, the caregiver is expected to record the patient's vital signs on a regular basis, and to record any reactions to the blood that the patient might experience. Reporting such reactions to the blood bank, and possibly on to the blood collection agency, may be appropriate to ensure that other patients are not similarly affected.

These procedures are fraught with latent errors. The original blood sample for matching the blood may be collected from the wrong patient, or may be mislabeled. The person picking up the blood unit from the blood bank may pick up the wrong blood unit. It may take too long to carry the blood unit to the patient, so that the blood has exceeded 30 minutes outside of refrigeration. There are even more risks during the transfusion process. The patient may not be wearing a suitable wristband providing positive patient identification, making it impossible for the caregiver to confirm that the blood unit is intended for that patient. The caregiver may misread the blood unit's unique identification number (which can be more 15 characters in length) when comparing it to the compatibility label. Errors may be made in transcribing the patient information or blood unit number into the patient record. The standard procedures for transfusion involve many steps that may be forgotten or not properly completed, particularly if the caregiver is expected to recall the procedure from memory.

Despite the best efforts of blood supply agencies, it is not uncommon for the trail of a blood unit to be lost as soon as it is delivered to a hospital blood bank. There may be records within the blood bank showing which patient a blood unit was prepared and tested for, but once again, the blood bank usually loses track of the blood unit once it leave the blood bank. Most blood banks assume that any blood units not returned to the blood bank have been transfused. Blood supply agencies assume that any blood delivered to a hospital blood bank was either transfused or wasted.

Although 'electronic issue' capability is common in blood bank software systems, the full potential of electronic issue is rarely used. By allocating blood for patients in advance, a large amount of blood is reserved, and hence unavailable for other patients. Electronic issue is intended to mitigate this by allowing blood to be allocated on a 'just in time' basis, however, as the blood units must be labeled for each patient, this is still done in the blood bank, meaning that even electronic issue must be done somewhat in advance of need so that there is time to collect the blood from the blood bank and transport it to the patient.

There are products that attempt to ensure that blood samples drawn from a patient for testing are correctly labeled. (e.g., Safe Track, DataLog International Ltd., www.dataloguk.com, BDID, Becton Dickinson Ltd, www.bd.com, McKesson Corporation, www.mckesson.com) These systems do a good job of making sure that the label applied to the blood sample collected from the patient match the information on the patient's wristband, but do not offer any improvement in the completion of the audit trail for the complete transfusion process.

There have also been attempts to improve the monitoring of the movement of blood units from place to place, to ensure that the blood is correctly stored, that all movements are recorded and that the blood does is not outside of refrigeration for more than the allowed time. (e.g., Blood Track, DataLog International Ltd., www.dataloguk.com). These systems provide valuable audit information for movements from one storage location to another, but lose track of the blood unit in the critical last step, when the blood unit is removed for transfusion. In addition, the systems rely on users to scan various barcodes in the correct order to ensure that the movement of the blood units is correctly recorded.

There have also been attempts to improve the transfusion process itself. There are products that use barcode scanners to compare bar-coded information on the patient's wristband, the compatibility label and the blood unit to ensure a correct match. (e.g., Safe Track, DataLog International Ltd, www.dataloguk.com, Itrac, Immucor, www.immucor.com). These products do provide a means for improving the safety of the transfusion step, but do not return information to the blood bank to confirm the completion of the transfusion or report reactions. They also fail to provide a means to ensure that the blood unit to be transfused has been stored and transported correctly and within the acceptable time limits. Thus, there remains a need in the art for improved apparatus and methods for ensuring reliable transfusion of blood and/or blood products into a specified patient.

SUMMARY OF THE INVENTION

The present invention fulfills these and related needs by providing apparatus and method for collecting and storing information relevant to the blood transfusion process for a patient, including information about the steps of collecting the blood sample, labelling the blood unit, collecting and transporting the blood unit, transfusing the blood unit, completion of the transfusion, and recording of any reactions that may have occurred. Within certain embodiments, the collected information is transmitted to a computer database so that a complete record of transfusion events can be created and maintained.

Thus, the present invention provides means for ensuring that a patient is correctly identified and that a blood sample collected from the patient is properly labelled. In another aspect, the invention ensures that a blood unit collected from a blood bank is associated with the intended patient and that the time elapsed between removal of the blood unit from refrigeration and transfusion or subsequent storage is properly recorded. In one embodiment of the invention, these recording steps are automatically performed with a minimum of actions required on the part of the person collecting the blood.

Other embodiments of the present invention provide means for comparing the information on a patient wristband and a compatibility label, and further comparing the information on the compatibility label with information on a blood unit to ensure a correct match between the patient, the compatibility label, and the blood unit. Within certain aspects, the invention also includes a means for recording the patient's vital signs, and for recording any adverse reactions the patient may have to the blood transfusion.

Further the invention provides means for reliably transmitting information to the computer database either through a computer network or without use of a computer network.

In addition, the invention provides means for presenting step-by-step instructions and reminders to the caregiver to ensure that all the critical steps of the transfusion process are completed in the right way.

The invention also provides a means to safely provide remote electronic issue of blood units for designated patients, reducing the amount of blood inventory required by the blood bank.

BRIEF DESCRIPTION OF THE DRAWINGS

These and other objects, features and advantages of the present invention will become apparent upon reference to the following detailed description of the exemplary embodiment presented herein and to the drawings wherein.

DETAILED DESCRIPTION OF THE INVENTION

Figure 1:
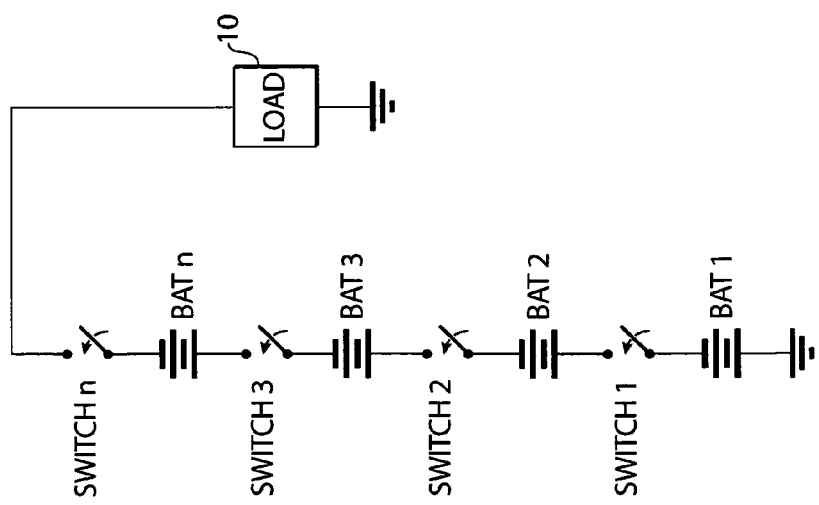
FIG. 1 illustrates a flowchart for transfusing blood products to a patient.

FIG. 1 illustrates one possible method for transfusing blood or a blood product into a patient, while storing transfusion information into transfusion database 10, in accordance with the invention. The transfusion method is best described in five steps, each of which is explained in more detail below.

The first step in the transfusion method is to collect a blood sample from the patient 12. This sample is tested to determine what type of blood is required for the patient. When the determination is complete, one or more blood units are allocated for the patient 14.

When a patient is determined to need a blood transfusion, a request is made for the blood unit or units allocated to the patient 16. The requested blood unit is transported to the patient's location 18, where it is transfused 20.

At each step in the process, certain information is recorded in transfusion database 10 so that a complete record of the transfusion event is available for review.

Figure 2:
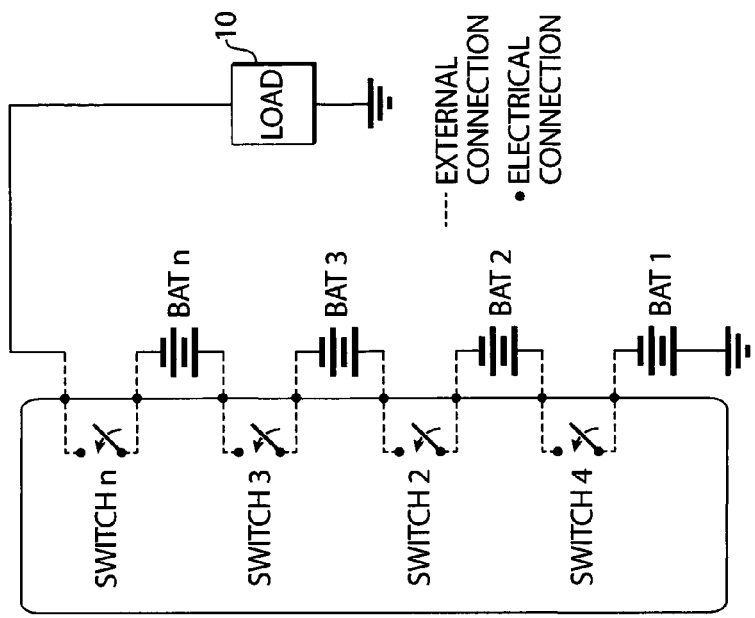
FIG. 2 is a schematic diagram of one possible apparatus for managing the sample collection, blood unit requesting and transfusion steps of FIG. 1.

FIG. 2 illustrates apparatus suitable for implementing the sample collection 12, Requesting 16 and transfusion 20 steps of the method according to the invention. The apparatus includes several components that are used in conjunction to execute the steps.

Each caregiver involved in the transfusion process has an identity means 110 which includes electronically readable caregiver code 112. Caregiver code 112 may be a linear or two-dimensional barcode using any one of many common barcode formats, such as code39, code128, Interleave 2 of 5, PDF 417, Matrix code, or others. Caregiver code 112 may also be any other type of electronically readable code means such as a Radio Frequency Identification (RFID) tag. Caregiver identity means 110 may be an employee identification card or similar item, in which caregiver code 112 is embedded, or to which caregiver code 112 is applied. In the exemplary embodiment presented herein, caregiver code 112 is a barcode or RFID label encoded with a unique number or letter combination, which is applied to the caregivers' employee identification.

Each patient to be transfused wears a patient identification wristband 114 which includes electronically readable patient code 116. Patient code 116 may be a linear or two-dimensional barcode using any one of many common barcode formats, such as code39, code128, Interleave 2 of 5, PDF 417, Matrix code, or others. Patient code 116 may also be any other type of electronically readable code means such as a Radio Frequency Identification (RFID) tag. In the exemplary embodiment presented herein, patient code 116 is a PDF-417 barcode or and RFID tag, in which the patient's identity number, surname, forename, date of birth and sex are encoded.

In the exemplary embodiment presented herein wristband 114 is either a PDC Smart CompuBand or PDC Smart ScanBand (Precision Dynamics Corporation, www.pdcorp.com). These wristbands incorporate RFID chips and can be programmed and printed with any standard barcodes using printers like the Zebra Technologies R402 printer/programmer (Zebra Technologies, www.zebra.com). Although one possible embodiment of the invention uses RFID wristbands, an alternative embodiment uses wristbands having printed barcodes and no RFID chips. Wristbands that may be printed with barcodes are available from many sources, including the Z-Band from Zebra technologies. The Z-Band and similar products can be printed using commonly available thermal and thermal transfer label printers.

The apparatus according to the invention also includes a portable computer, preferably a Personal Digital Assistant (PDA) 118. PDA 118 includes reader 120 which is able to read caregiver code 112 and patient code 116. Reader 120 may be a barcode scanner, a barcode imager or an RFID reader. PDA 118 is also preferably equipped with a wireless network means, a touch screen, communication means for communicating with a portable printer, and is suitable for cleaning and disinfection. In the exemplary embodiment presented herein, PDA 118 is a Symbol PPT2748, a Symbol SPT1746, a Symbol MC50, a Symbol MC3000 (Symbol Technologies Ltd, www.symbol.com), an HHP Dolphin, or an Intermec Model 700.

Included on PDA 118 is software to implement the sample collection 12, requesting 16 and transfusion 20 methods in accordance with the invention, as hereinafter described.

The apparatus further includes portable printer means 124 which can communicate with PDA 118 such that PDA 118 can cause printer 124 to print labels as required. In the exemplary embodiment presented herein, printer 124 is a Zebra QL-220 (Zebra Technologies, www.zebra.com) battery powered printer which may be connected to PDA 118 with a cable.

Figure 3:
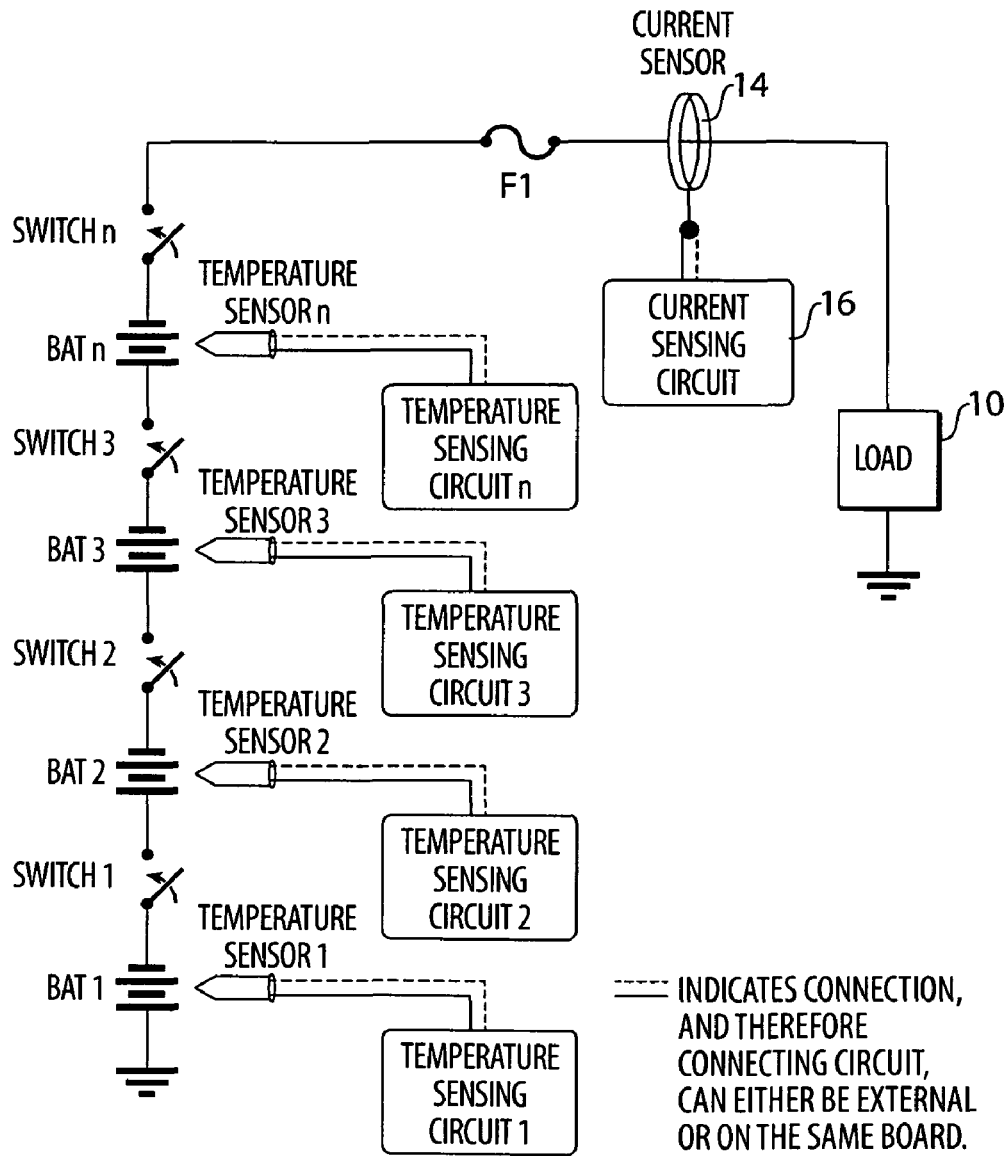
FIG. 3 illustrates a flowchart for the sample collection step of FIG. 1.

Referring to FIG. 3, software included on PDA 118 provides means for performing the sample collection process 12. At each step in sample collection process 12, the software causes PDA 118 to display messages to the caregiver indicating the next step that the caregiver should perform. This forces the caregiver to follow a pre-defined procedure that is the same each time sample collection process 12 is performed. This has the effect of allowing even inexperienced caregivers to perform a complex task as if they have been highly trained.

In the first step of sample collection process 12, PDA 118 displays a message asking the caregiver to read their caregiver code 112 (step 22). To do this, the caregiver uses reader 120 of PDA 118 and either scans caregiver code 112 (if caregiver code 112 is a barcode) or brings reader 120 within range of caregiver code 112 (if caregiver code 112 is an RFID tag). PDA 118 displays caregiver code 112 so that the caregiver can verify it.

Next, PDA 118 displays a message requesting the caregiver to read patient code 116 (step 24). Using reader 120 of PDA 118, the caregiver either scans patient code 116 (if patient code 116 is a barcode) or brings reader 120 within range of patient code 116 (if patient code 116 is an RFID tag). PDA 118 displays the patient identification information encoded in patient code 116. In the exemplary embodiment presented herein, this display includes the patient's identification number, surname, forename, date of birth and sex. PDA 118 displays a message asking the caregiver to confirm that the patient information is correct. Caregivers are expected to ask the patient their name and date of birth to ensure that the displayed information is correct before proceeding with sample collection.

If the caregiver is satisfied that the information read from wristband 114 is correct, they press a button on PDA 118 to confirm that they have checked the information.

PDA 118 now displays a selection of tests for the caregiver to request for the blood sample. The caregiver presses the appropriate buttons on PDA 118 to indicate the tests they wish to have performed (step 25). In some situations, the tests required for a blood transfusion are pre-determined and PDA 118 will automatically assign the tests and move to the next step.

PDA 118 then displays a button for printing. The caregiver connects PDA 118 to printer 124 and presses the print button, which causes printer 124 to produce sample label 122 (step 26). A timer within PDA 118 prevents the caregiver from printing label 122 if more than a pre-set time (typically 15 to 30 seconds) has passed since patient code 116 was read. This encourages the caregiver to print the sample label while at the patient's bedside, rather than at a later time when there is some chance that the label may be mixed up with other labels or applied to the wrong sample.

Sample label 122 shows the patient identification information read from patient code 116, the type of test required on the sample, and may include a barcode encoding all or some of this information. In the exemplary embodiment presented herein, label 122 includes a PDF-417 two-dimensional barcode which encodes the patient's identification number, surname, forename, date of birth and sex, as well as a code representing the test required, caregiver code 112, the time and date, and a unique identifier for PDA 118.

The caregiver now collects the required blood sample, following standard blood sample collection techniques (Step 28). Once the sample is collected into the collection container, label 122 is applied to the container (step 30).

PDA 118 now displays a button which allows the caregiver to confirm that the sample collection is complete. At this point, PDA 118 transmits a record to transfusion database 10, recording the collection of the blood sample (step 32). There are two ways in which this information can be transmitted to transfusion database 10. In the exemplary embodiment presented herein, PDA 118 incorporates a wireless network connection (which may be an IEEE 802.11b wireless network connection or other similar wireless network connection). If available, this wireless network connection is used by the software included on PDA 118 to insert the sample collection record into transfusion database 10.

In an alternative embodiment, PDA 118 is not equipped with a wireless network connection, or there is no wireless network available at the location where the blood sample is collected. In this case, the software on PDA 118 causes a second copy of label 122 to be printed by printer 124. This second label, which in this embodiment includes a PDF-417 two-dimensional barcode as described above, is taken to a computer connected to transfusion database 10. This computer is equipped with a barcode reader capable of reading the PDF-417 barcode and inserting the information read into transfusion database 10.

Once the blood sample is collected and labelled, it is transported to the blood bank laboratory for testing (step 34).

Figure 4:
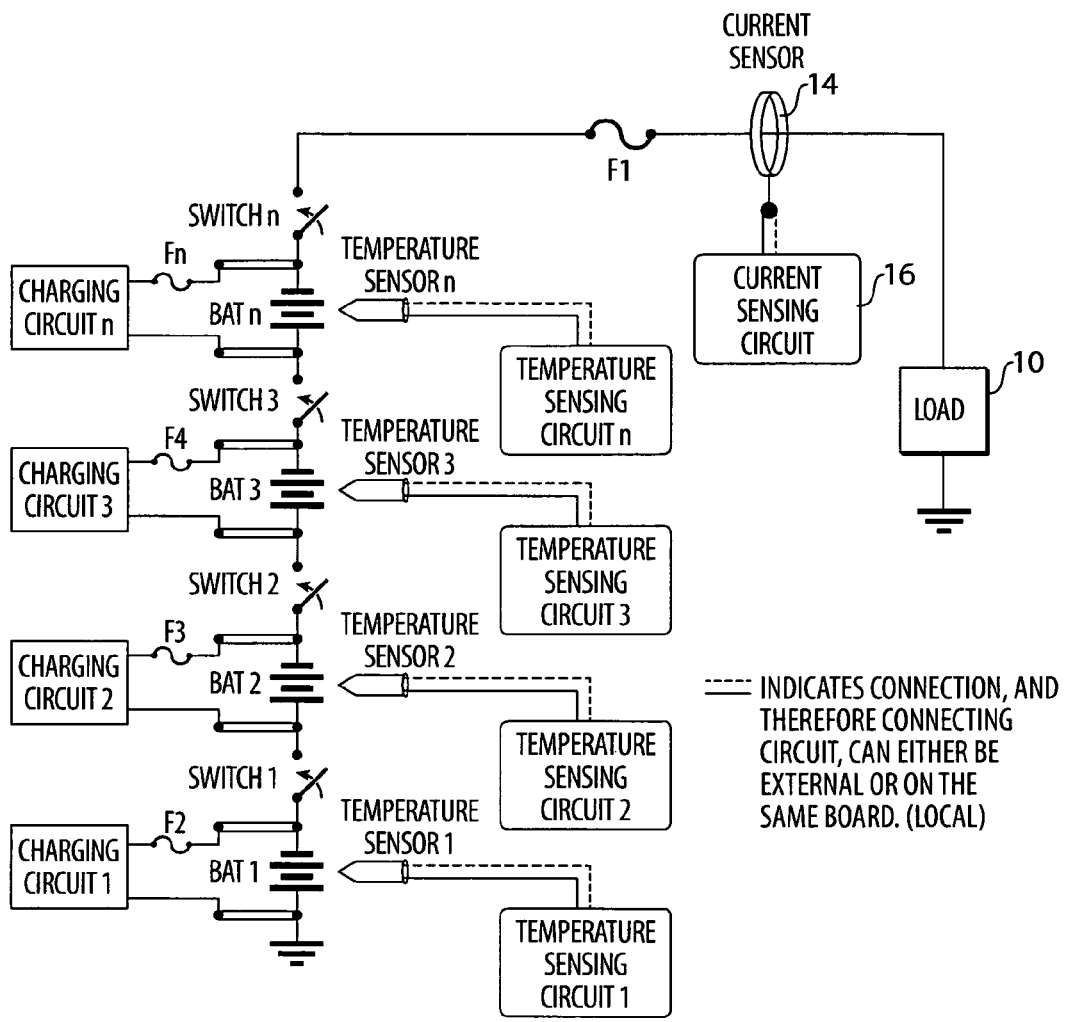
FIG. 4 illustrates a flowchart for the sample testing and blood unit allocation step of FIG. 1.

FIG. 4 illustrates the procedures followed in the blood bank laboratory in preparation for a blood transfusion (step 14, FIG. 1). The exact procedure followed by a specific laboratory may vary, so the following procedure should be taken as one possible example only.

Blood units collected by a blood collection agency are received by the blood bank (step 40). The unique identification, type and other information about each blood unit are recorded.

Blood bank laboratories may do their own tests on received blood to confirm the type of blood or to ascertain other special characteristics of the blood (step 42). Once these tests are completed, the blood units are placed into storage within the blood bank (step 44), where they await assignment to a particular patient.

When the blood bank laboratory receives a blood sample collected for a patient (step 46), it is tested to determine the specific requirements for the patient (step 50). These tests will determine the patient's blood type (A, B, O) and Rhesus Factor and determine if there are any other particular requirements for the patient, such as antibody negative, irradiated, or CMV Negative blood.

Once the test results are known, an appropriate blood unit for the patient is selected from the stored blood units (step 50).

The unique identification number of the selected blood unit and the patient identification as determined from the blood sample collected from the patient are printed on a compatibility label (step 52). In accordance with the invention, this label also includes an electronically readable compatibility code, which may be a linear or two-dimensional barcode or other electronically readable code means such as a Radio Frequency Identification (RFID) tag. Encoded in the barcode or RFID tag are the patient identification and unique identification number of the blood unit. Standard blood transfusion practice dictates that there be at least three separate items of patient identification included in the compatibility information, such as the patient ID number, surname and date of birth.

The printed compatibility label is applied to the selected blood bag (step 54), after which the labelled blood bag is placed into an appropriate storage location for pickup when required (step 56). When the blood unit is placed into the storage location for pickup, records are inserted into transfusion database 10. This record includes the time and date, the unique identification number of the selected blood unit, the patient's identification, and may include additional information such as the sample number assigned to the blood sample drawn from the patient, the results of the tests done in the blood bank laboratory, the blood type selected and the specific characteristics of the blood unit assigned.

Figure 5:
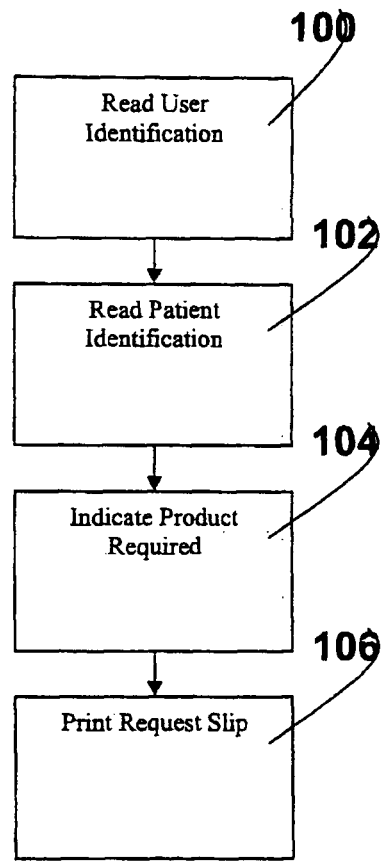
FIG. 5 is a flowchart for the blood unit requesting step of FIG. 1.

FIG. 5 illustrates the process for requesting a blood unit for a particular patient from the blood bank (FIG. 1 step 16). This procedure uses the apparatus illustrated in FIG. 2.

When a caregiver wants to obtain a blood unit for transfusion, they must create a request document to positively identify the patient for whom the blood is needed, so that the person collecting the blood can be sure to collect the correct blood unit for the patient.

In the first step of blood unit requesting process (FIG. 1 step 14), PDA 118 displays a message asking the caregiver to read their caregiver code 112 (step 100). To do this, the caregiver uses reader 120 of PDA 118 and either scans caregiver code 112 (if caregiver code 112 is a barcode) or brings reader 120 within range of caregiver code 112 (if caregiver code 112 is an RFID tag). PDA 118 displays caregiver code 112 so that the caregiver can verify it.

Next, PDA 118 displays a message requesting the caregiver to read patient code 116 (step 102). Using reader 120 of PDA 118, the caregiver either scans patient code 116 (if patient code 116 is a barcode) or brings reader 120 within range of patient code 116 (if patient code 116 is an RFID tag). PDA 118 displays the patient identification information encoded in patient code 116. In the exemplary embodiment presented herein, this display includes the patient's identification number, surname, forename, date of birth and sex. PDA 118 displays a message asking the caregiver to confirm that the patient information is correct. Caregivers are expected to ask the patient their name and date of birth to ensure that the displayed information is correct before proceeding with sample collection.

If the caregiver is satisfied that the information read from wristband 114 is correct, they press a button on PDA 118 to confirm that they have checked the information.

PDA 118 now displays a selection of blood products that a caregiver might require for the patient. This is most commonly Red Cells, but may be Platelets, Flash Frozen Plasma, or other blood products. The caregiver presses the appropriate buttons on PDA 118 to indicate the blood product they require (step 104). In some situations, the system may be used for ordering only one type of blood product, in which case PDA 118 will automatically assign the product type and move to the next step.

PDA 118 then displays a button for printing. The caregiver connects PDA 118 to printer 124 and presses the print button, which causes printer 124 to produce request slip 122 (step 106).

Request slip 122 shows the patient identification information read from patient code 116, the type of blood product required and may include a barcode encoding all or some of this information. In the exemplary embodiment presented herein, request slip 122 includes a PDF-417 two-dimensional barcode which encodes the patient's identification number, surname, forename, date of birth and sex, as well as a code representing the blood product required, required, caregiver code 112, the time and date, and a unique identifier for PDA 118.

The request slip printed in step 106 is given to a person responsible for collecting the patient's blood from the blood bank refrigerator.

Figure 6:
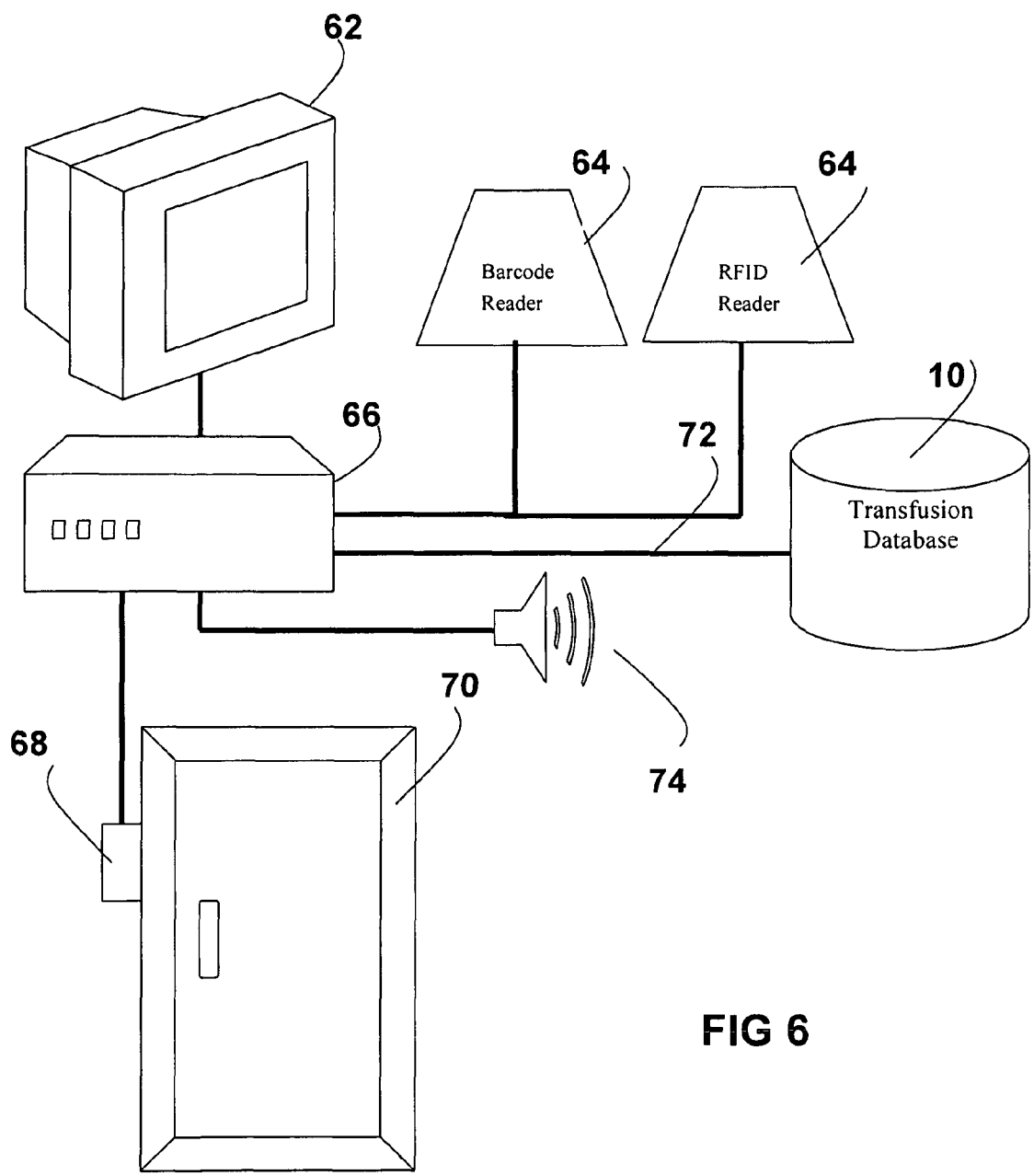
FIG. 6 is a schematic diagram of one possible apparatus for managing the blood unit transportation step of FIG. 1, in accordance with the present invention.

FIG. 6 illustrates apparatus suitable for implementing the transportation of allocated blood to the patient (FIG. 1 step 18).

Blood products assigned to a particular patient are stored in refrigerator 70, which is usually in a location accessible to those charged with collecting blood for patients. Refrigerator 70 is equipped with electronic lock 68, which in turn is connected to computer 66, such that software installed on computer 68 can lock and unlock refrigerator 70.

Also connected to computer 66 is reader 64, which may be a barcode scanner or RFID reader. Computer 66 is also connected to speaker 74, and transfusion database 10. Transfusion database 10 may be on a hard disk drive installed within computer 66, or may be on a data storage device connected to computer 66 via computer network connection 72 as illustrated in FIG. 6.

Computer 66 is further connected to touch screen 62 that provides a visual display and a touch operated user interface for operating the software operating on computer 66.

In many hospitals where transfusions are performed, there are several refrigerators where blood designated for a particular patient may be stored. Blood assigned for a particular patient at the blood bank may be moved from the blood bank refrigerator to another refrigerator closer to the patient before it is finally collected for transfusion. Blood removed from the refrigerator for transfusion may not be used and will be returned for use at a later time. In each case, it is important that the blood not be out of refrigeration for longer than an acceptable time, and that any blood that has been out of refrigeration for too long not be used.

For these reasons, the apparatus illustrated in FIG. 6 should normally be installed at every location where blood it to be stored, even temporarily. Each such installation will be connected to transfusion database 10 so that data is shared among all instances of the apparatus.

Figure 7A:
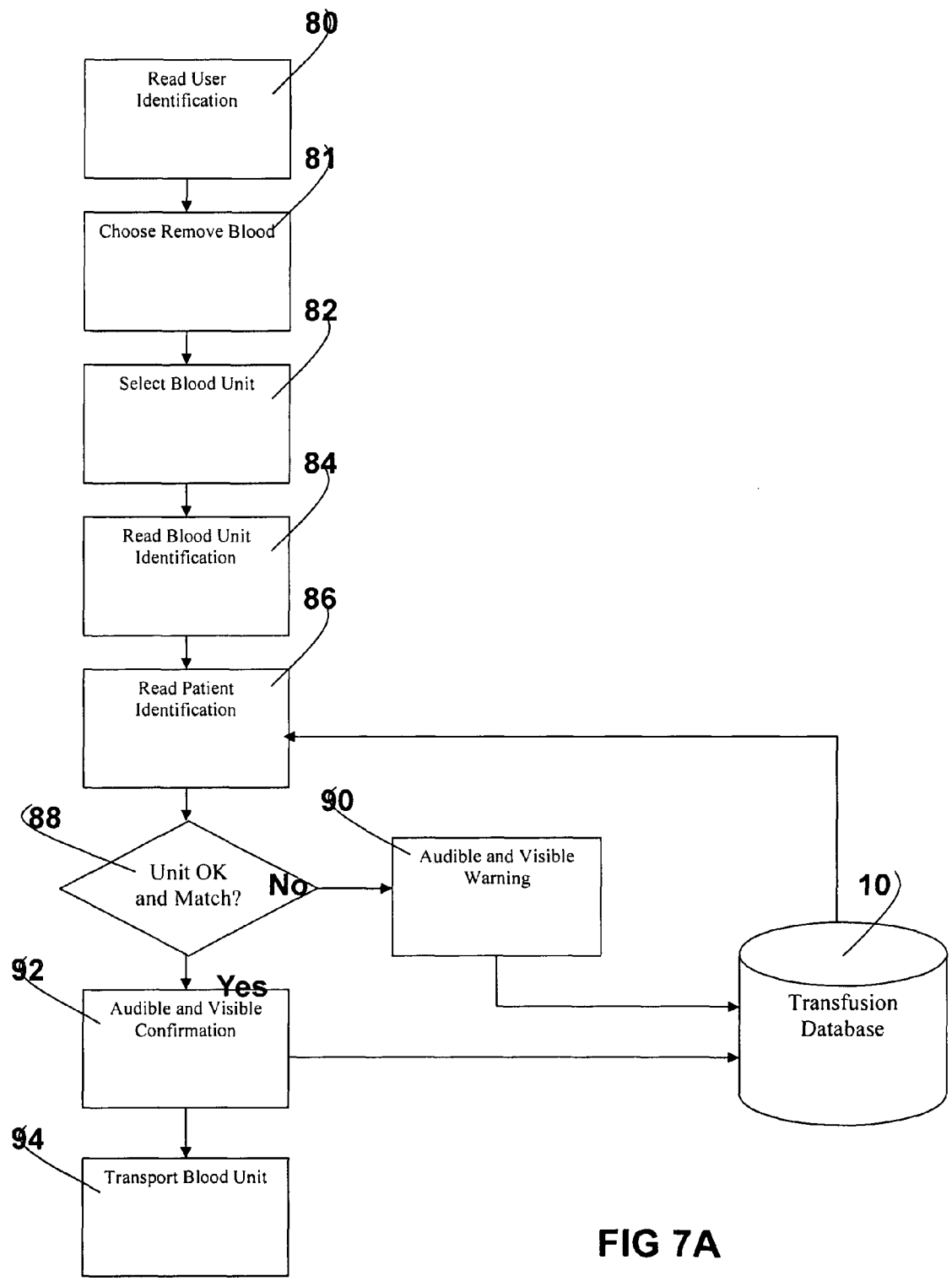
FIG. 7A-7D are flowcharts for the blood unit transportation step of FIG. 1 using the apparatus of FIG. 6 (FIG. 7A) and for returning blood to storage if it is not transfused, using the apparatus of FIG. 6 (FIG. 7B).

FIG. 7A illustrates how the apparatus of FIG. 6 is used when collecting blood from a refrigerator for transfusion.

In one embodiment of the invention, reader 64 of FIG. 6 is a barcode scanner capable of reading both linear and two-dimensional barcodes. In an alternative embodiment, reader 64 is an RFID reader. In the latter case, the receiving antennas of RFID reader 64 are located both inside refrigerator 70 and near the door of refrigerator 70, and are disposed so that any RFID tags located inside refrigerator 70 or near the outside of refrigerator 70 may be read. Operation of the two different embodiments of the invention will be described separately.

In the first embodiment of the invention, referring to FIG. 7A, the caregiver collecting a blood unit identifies themselves by scanning the caregiver code 112 on their caregiver identification 110, using reader 64, which in this embodiment is a barcode reader (step 80). Software located on computer 66 determines if the caregiver identified by caregiver code 112 is authorized to collect blood units, and if so, displays two buttons on touch screen 62. The caregiver touches the appropriate button to indicate that they intend to remove blood from the refrigerator (step 81).

The software on computer 66 uses speaker 74 and the display of touch screen 62 to ask the caregiver to select the blood unit they wish to remove, and unlocks lock 68 so that the caregiver can open refrigerator 70. The caregiver selects the blood upon labelled with a compatibility label matching the patient for whom they are collecting the blood. The caregiver then closes refrigerator 70 and reads a barcode on the blood unit that uniquely identifies the blood unit, or the compatibility label on the blood unit (step 84), using reader 64.

The software on computer 66 now uses touch screen 62 uses speaker 74 to request the caregiver to read the request slip printed when blood was requested for the patient (FIG. 1 step 16). The caregiver uses reader 64 to read the two-dimensional barcode on the request slip (step 86). The software on computer 66 retrieves records from transfusion database 10 to determine if the blood is still useable, and if so, retrieves records from transfusion database 10 to determine which patient the blood unit was assigned to, and compares this information to that encoded on the request slip. If the information matches and the blood unit is still useable (step 88), the software on computer 66 uses speaker 74 and touch screen 62 to provide confirmation that the correct blood unit has been selected (step 92). If the information does not match or the blood is not useable in step 88, the software on computer 66 uses speaker 74 and touch screen 62 to warn the caregiver that the wrong blood was selected, and instructs them to replace the blood unit into refrigerator 70 and select the correct blood unit (step 90).

As soon as the information is checked in step 88, a record of the transaction is written into transfusion database 10. Recording errors made by the caregiver assists in corrective training and resolution of the sources of error.

Once the caregiver has selected the correct blood unit and verified it, the software on computer 66 engages lock 68 on refrigerator 70 and returns to a state in which caregiver identification codes may be read to start the process again.

The caregiver may now transport the blood unit either to the patient for transfusion, or to another refrigerator for further storage prior to transfusion (step 94).

Figure 7B:
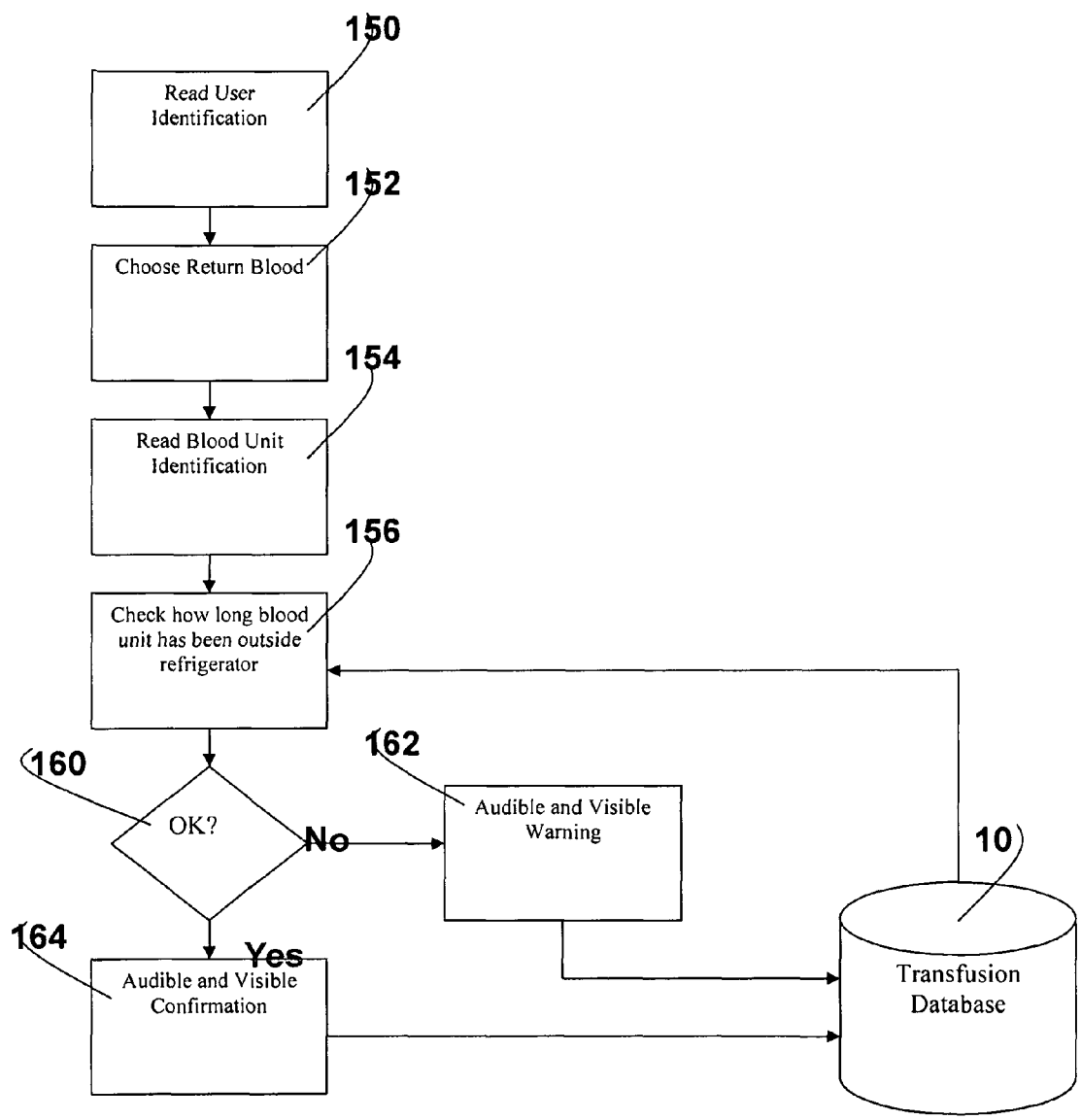

Should the blood unit need to return to storage in the same or another refrigerator 70, the process illustrated in FIG. 7B is followed.

First, the caregiver returning a blood unit identifies themselves by scanning the caregiver code 112 on their caregiver identification 110, using reader 64, which in this embodiment is a barcode reader (step 150). Software located on computer 66 determines if the caregiver identified by caregiver code 112 is authorized to return blood units, and if so, displays two buttons on touch screen 62. The caregiver touches the appropriate button to indicate that they intend to return blood to refrigerator 70 (step 152).

The software on computer 66 uses speaker 74 and the display of touch screen 62 to ask the caregiver to read the barcode on the blood unit that uniquely identifies the blood unit, or the compatibility label on the blood unit (step 154), using reader 64. Computer 66 unlocks lock 68 so that the caregiver can place the blood unit into refrigerator 70.

The software on computer 66 retrieves records from transfusion database 10 to determine when the blood unit was removed from refrigeration (step 156). It then calculates the time that the blood unit has been outside of refrigeration and compares the calculated time with the pre-set allowable time limits (step 160). If the blood unit has not been outside of refrigeration for more than the allotted time, the software on computer 66 uses speaker 74 and touch screen 62 to give a confirmation message to the caregiver (step 164). If the blood unit has been outside of refrigeration for longer than the allotted time, the software on computer 66 uses speaker 74 and touch screen 62 to give a warning message to the caregiver (step 162).

As soon as the information is checked in step 160, a record of the transaction is written into transfusion database 10. If the blood unit has exceeded its allowable time outside of refrigeration, the record is marks the blood unit as unusable. The software on computer 66 then engages lock 68 on refrigerator 70 and returns to a state in which caregiver identification codes may be read to start the process again.

In the second exemplary embodiment presented herein of the invention, reader 64 is an RFID reader, and the compatibility label on the blood unit includes an RFID tag, as does the request slip prepared in the blood requesting procedure (FIG. 1, step 18).

Figure 7C:
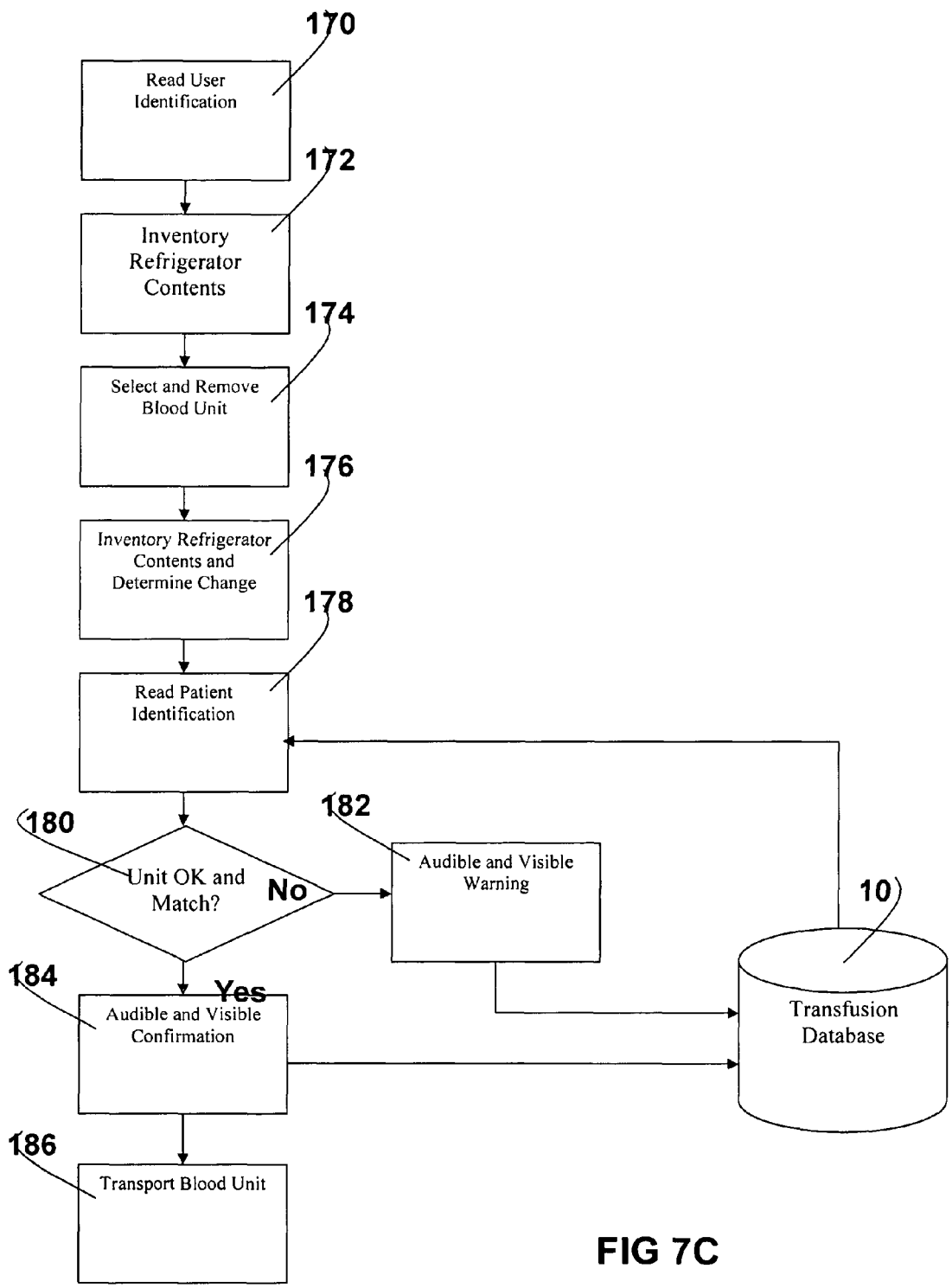

As illustrated in FIG. 7C, the procedure for removing a blood unit from refrigerator 70 in the alternative embodiment is somewhat different from previously described.

First, reader 64 reads caregiver code 112 located on the caregiver's identification 110 as soon as the caregiver's identification 110 is within range of reader 64 (step 170). As the antenna for RFID reader 64 is disposed to read RFID tags near refrigerator 70, this alerts the software located on computer 66 that a caregiver many want to remove blood from refrigerator 70. The software on computer 66 then instructs reader 66 to read the RFID tags on every blood unit inside refrigerator 70 in order to establish an inventory of all blood units currently inside refrigerator 70 (step 172). Once this inventory is complete, computer 66 disengages lock 68 so that the caregiver may select a blood unit for removal (step 174). The software on computer 66 then instructs reader 66 to read the RFID tags on every blood unit inside refrigerator 70 in order to establish an inventory of all blood units remaining inside refrigerator 70 (step 176). The inventory from step 176 is compared to the inventory from step 172 to determine which blood unit was removed by the caregiver. As soon as the identity of the removed blood unit is established, the software on computer 66 retrieves records from transfusion database 10 to determine the identity of the patient for which the blood bag is intended, and to determine if the blood unit is still useable.

The software on computer 66 then instructs reader 64 to read the RFID tagged request slip prepared during the requesting step (FIG. 1, step 16). The software compares the patient identification retrieved from transfusion database 10 and the data read from the request slip to determine if the two match and if the blood unit is still useable (step 180). If the information matches and the blood unit is still useable the software on computer 66 uses speaker 74 and touch screen 62 to provide confirmation that the correct blood unit has been selected (step 184). If the information does not match or the blood is not useable in step 88, the software on computer 66 uses speaker 74 and touch screen 62 to warn the caregiver that the wrong blood was selected, and instructs them to replace the blood unit into refrigerator 70 and select the correct blood unit (step 182).

As soon as the information is checked in step 180, a record of the transaction is written into transfusion database 10. Recording errors made by the caregiver assists in corrective training and resolution of the sources of error.

Once the caregiver has selected the correct blood unit and verified it, the software on computer 66 engages lock 68 on refrigerator 70 and returns to a state in which caregiver identification codes may be read to start the process again.

The caregiver may now transport the blood unit either to the patient for transfusion, or to another refrigerator for further storage prior to transfusion (step 186).

Figure 7D:
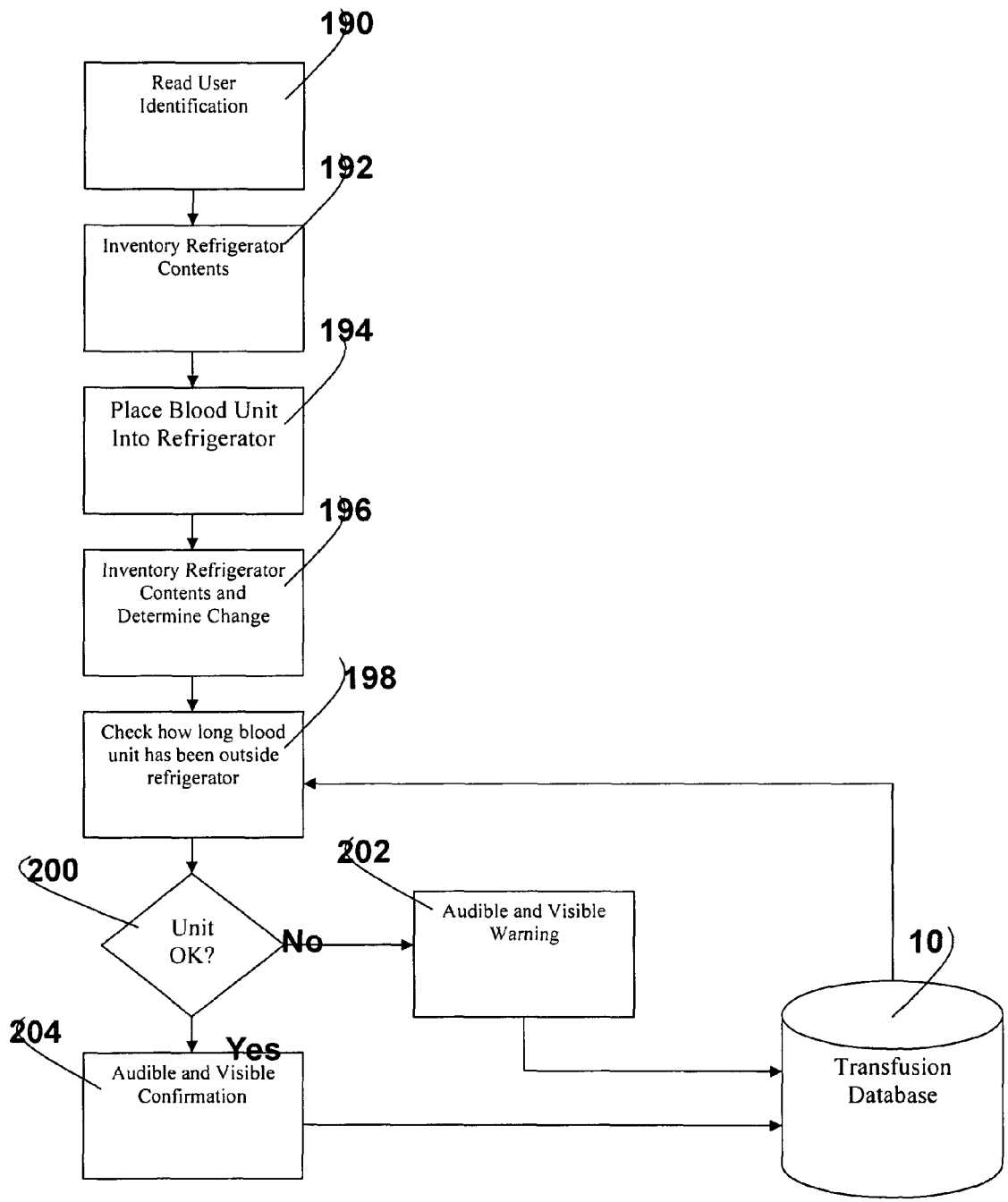

Should the blood unit need to return to storage in the same or another refrigerator 70, the process illustrated in FIG. 7D is followed in the case of the alternative embodiment.

First, reader 64 reads caregiver code 112 located on the caregiver's identification 110 as soon as the caregiver's identification 110 is within range of reader 64 (step 190). As the antenna for RFID reader 64 is disposed to read RFID tags near refrigerator 70, this alerts the software located on computer 66 that a caregiver many want to return blood to refrigerator 70. The software on computer 66 then instructs reader 66 to read the RFID tags on every blood unit inside refrigerator 70 in order to establish an inventory of all blood units currently inside refrigerator 70 (step 192). Once this inventory is complete, computer 66 disengages lock 68 so that the caregiver may put the blood unit back inside refrigerator 70 (step 194). The software on computer 66 then instructs reader 66 to read the RFID tags on every blood unit inside refrigerator 70 in order to establish an inventory of all blood units now inside refrigerator 70 (step 196). The inventory from step 196 is compared to the inventory from step 192 to determine which blood unit was added by the caregiver.

As soon as the identity of the removed blood unit is established, the software on computer 66 retrieves records from transfusion database 10 to determine when the blood unit was removed from refrigeration (step 198). It then calculates the time that the blood unit has been outside of refrigeration and compares the calculated time with the pre-set allowable time limits (step 200). If the blood unit has not been outside of refrigeration for more than the allotted time, the software on computer 66 uses speaker 74 and touch screen 62 to give a confirmation message to the caregiver (step 202). If the blood unit has been outside of refrigeration for longer than the allotted time, the software on computer 66 uses speaker 74 and touch screen 62 to give a warning message to the caregiver (step 204).

As soon as the information is checked in step 200, a record of the transaction is written into transfusion database 10. If the blood unit has exceeded its allowable time outside of refrigeration, the record is marks the blood unit as unusable. The software on computer 66 then engages lock 68 on refrigerator 70 and returns to a state in which caregiver identification codes may be read to start the process again.

It can be seen from the description for the two embodiments of the apparatus illustrated in FIG. 6, that the embodiment in which reader 64 is an RFID reader provides a much simpler set of actions by the caregiver. The RFID embodiment of the invention requires few specific actions on the part of the caregiver to ensure that the blood units are properly tracked and checked.

Figure 8:
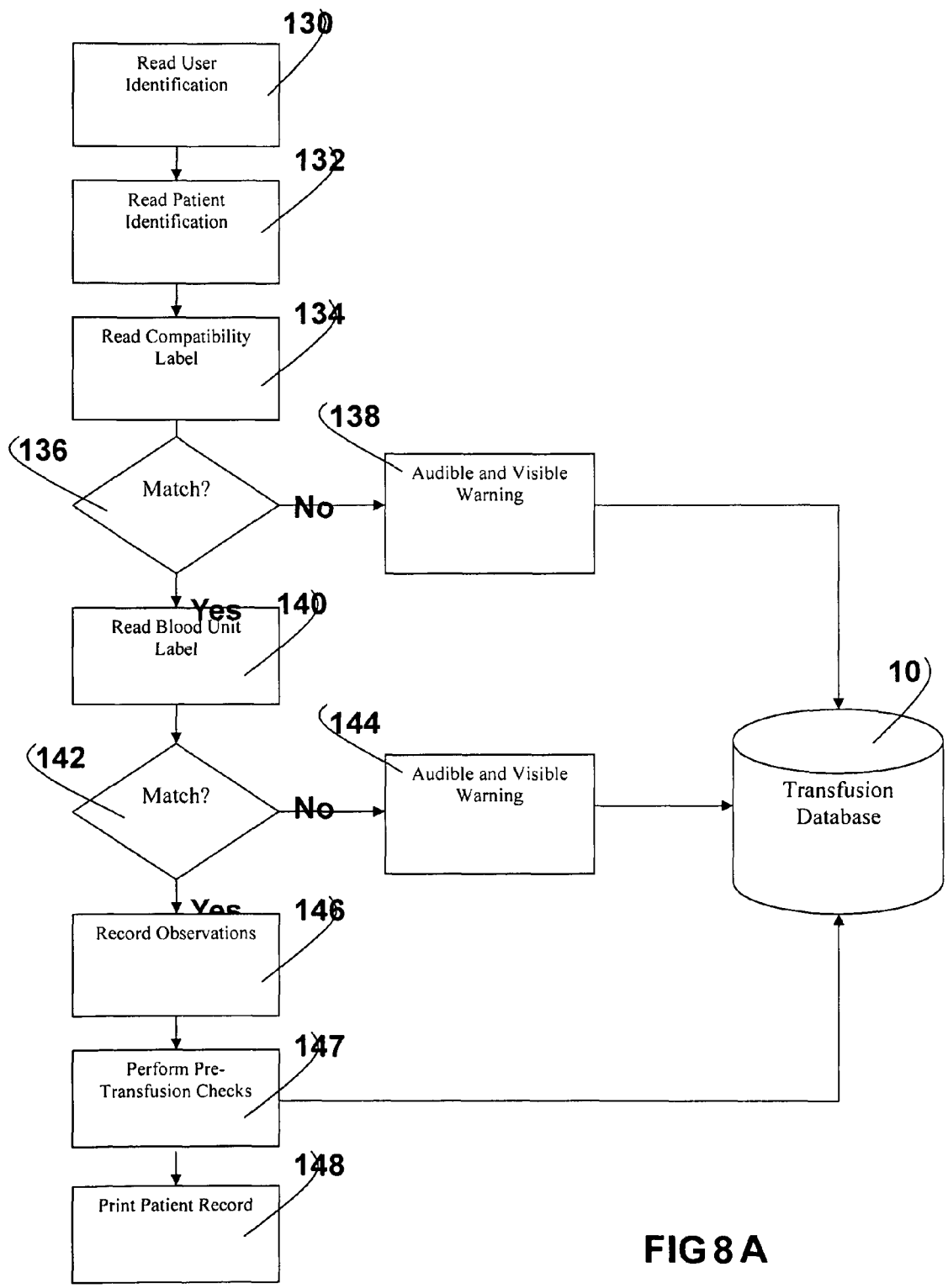
FIGS. 8A-8C are flowcharts for the transfusion step of FIG. 1, showing the steps for beginning a transfusion (FIG. 8A), for the transfusion step of FIG. 1, showing the steps for recording observations or reactions (FIG. 8B), and for the transfusion step of FIG. 1, showing the steps for completing a transfusion (FIG. 8C).

FIG. 8A illustrates the procedure for transfusing blood into a patient, using the apparatus depicted in FIG. 2.

Software included on PDA 118 provides means for performing the blood transfusion process (FIG. 1, step 20). At each step in the transfusion process, the software causes PDA 118 to display messages to the caregiver indicating the next step that the caregiver should perform. This has the effect of forcing the caregiver to follow a pre-defined procedure that is the same each time blood transfusion process 20 is performed. This has the effect of allowing even inexperienced caregivers to perform the critical transfusion task as if they have been highly trained.

In the first step of sample transfusion process 20, PDA 118 displays a message asking the caregiver to read their caregiver code 112 (step 130). To do this, the caregiver uses reader 120 of PDA 118 and either scans caregiver code 112 (if caregiver code 112 is a barcode) or brings reader 120 within range of caregiver code 112 (if caregiver code 112 is an RFID tag). PDA 118 displays caregiver code 112 so that the caregiver can verify it.

Next, PDA 118 displays a message requesting the caregiver to read patient code 116 (step 132). Using reader 120 of PDA 118, the caregiver either scans patient code 116 (if patient code 116 is a barcode) or brings reader 120 within range of patient code 116 (if patient code 116 is an RFID tag). PDA 118 displays the patient identification information encoded in patient code 116. In the exemplary embodiment presented herein, this display includes the patient's identification number, surname, forename, date of birth and sex. PDA 118 displays a message asking the caregiver to confirm that the patient information is correct. Caregivers are expected to ask the patient their name and date of birth to ensure that the displayed information is correct before proceeding with transfusion.

If the caregiver is satisfied that the information read from wristband 114 is correct, they press a button on PDA 118 to confirm that they have checked the information.

PDA 118 now displays a message asking the caregiver to read the compatibility label on the blood unit (step 134). Once again, the caregiver uses reader 120 of PDA 118 and either scans the compatibility label (if the compatibility label includes a barcode) or brings reader 120 within range of the compatibility label (if the compatibility label includes an RFID tag). PDA 118 displays the information encoded on the compatibility label along with the patient information already read, so that that caregiver can compare the patient information from both sources. If the information appears to be the same, the caregiver presses a button on PDA 118 to confirm that they have checked the information. This ensures that the right blood unit has been selected for the patient.

Before proceeding to the next step in the transfusion process, the software on PDA 118 compares the patient information read from patient code 116 on wristband 114 with the patient information read from the compatibility label (step 136). If the information does not match, PDA 118 displays a warning message and emits a warning sound (step 138). A record is inserted into transfusion database 10 that includes the information read from patient wristband 114 and the compatibility label and recording that the wrong blood unit was selected for the patient. The program on PDA 118 will not permit the caregiver to continue with the transfusion steps if the information does not match.

If the information read from patient code 116 and the compatibility label on the blood unit match, the software on PDA 118 displays a message asking the caregiver to read the blood unit label (step 140). Once again, the caregiver uses reader 120 of PDA 118 and either scans the blood unit label (if the blood unit label includes a barcode) or brings reader 120 within range of the blood unit label (if the blood unit label includes an RFID tag). PDA 118 displays the information encoded on the blood unit label along with the patient blood unit information already read from the compatibility label, so that that caregiver can compare the blood unit identification from both sources. If the information appears to be the same, the caregiver presses a button on PDA 118 to confirm that they have checked the information. This ensures that the compatibility label has been placed on the right blood unit.

Before proceeding to the next step in the transfusion process, the software on PDA 118 compares the blood unit information read from the compatibility label with the blood unit information read from the blood unit label (step 142). If the information does not match, PDA 118 displays a warning message and emits a warning sound (step 144). A record is inserted into transfusion database 10 that includes the information read from blood unit and the compatibility label and recording that the compatibility label was placed on the wrong blood unit. The program on PDA 118 will not permit the caregiver to continue with the transfusion steps if the information does not match.

Provided that the blood unit label and compatibility label match, the software on PDA 118 displays a message asking the caregiver to enter the patient's vital signs prior to starting the transfusion (step 146). These vital signs usually include the patient's blood pressure, pulse and temperature.

Once the vital signs are recorded, the software on PDA 118 displays a message asking the caregiver to confirm that various pre-transfusion checks have been completed (step 147). PDA 118 requires that the caregiver press a button next to each of these reminders to confirm that these pre-transfusion checks have been completed.

PDA 118 now displays a button which allows the caregiver to confirm that the blood transfusion has started. At this point, PDA 118 transmits a record to transfusion database 10, recording the start of the transfusion. There are two ways in which this information can be transmitted to transfusion database 10. In the exemplary embodiment presented herein, PDA 118 incorporates a wireless network connection (which may be an IEEE 802.11b wireless network connection or other similar wireless network connection). If available, this wireless network connection is used by the software included on PDA 118 to insert the transfusion start record into transfusion database 10. The transfusion start record includes the patient identification information read from patient code 116, the patient information and blood unit information read from the compatibility label, the blood unit information read from the blood unit label, caregiver code 112, the time and ate and a unique identifier for PDA 118.

At this stage, PDA 118 also displays a button for printing. The caregiver connects PDA 118 to printer 124 and presses the print button, which causes printer 124 to produce patient record label 122 (step 148). Patient record label 122 shows the patient identification, caregiver code 112, the blood unit number and the time and date. Patient record label 122 may also include a barcode encoding some or all of this information. In the exemplary embodiment presented herein, the printed patient record includes a PDF-417 two-dimensional barcode which encodes the patient identification information read from patient code 116, the patient information and blood unit information read from the compatibility label, the blood unit information read from the blood unit label, caregiver code 112, the time and date and a unique identifier for PDA 118.

In an alternative embodiment, PDA 118 is not equipped with a wireless network connection, or there is no wireless network available at the location where the blood transfusion is started. In this case, the software on PDA 118 causes a second copy of patient record label 122 to be printed by printer 124. This second label, which in this embodiment includes a PDF-417 two-dimensional barcode as described above, is taken to a computer connected to transfusion database 10. This computer is equipped with a barcode reader capable of reading the PDF-417 barcode and inserting the information read into transfusion database 10.

Figure 8B:
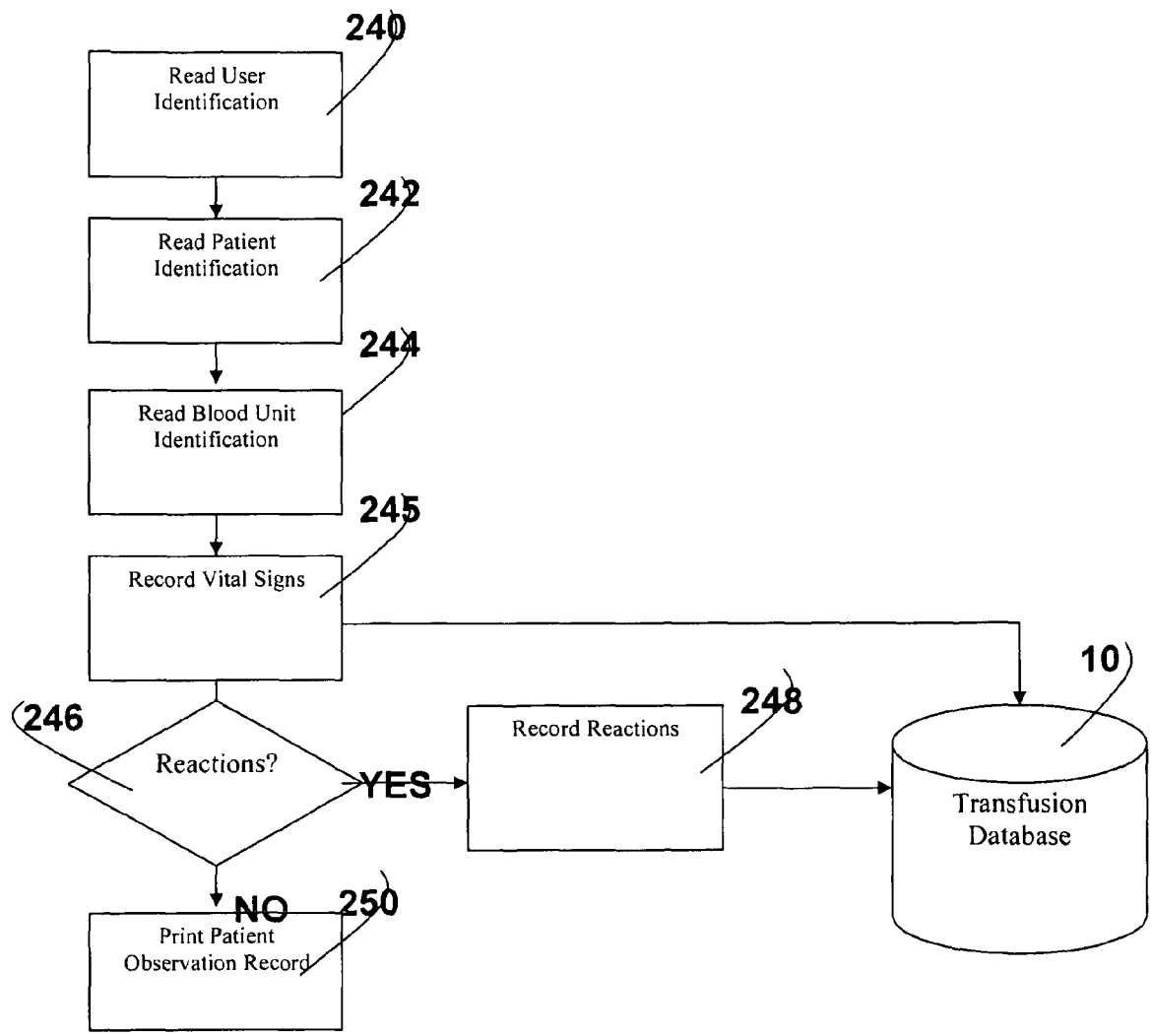
Figure 8C:
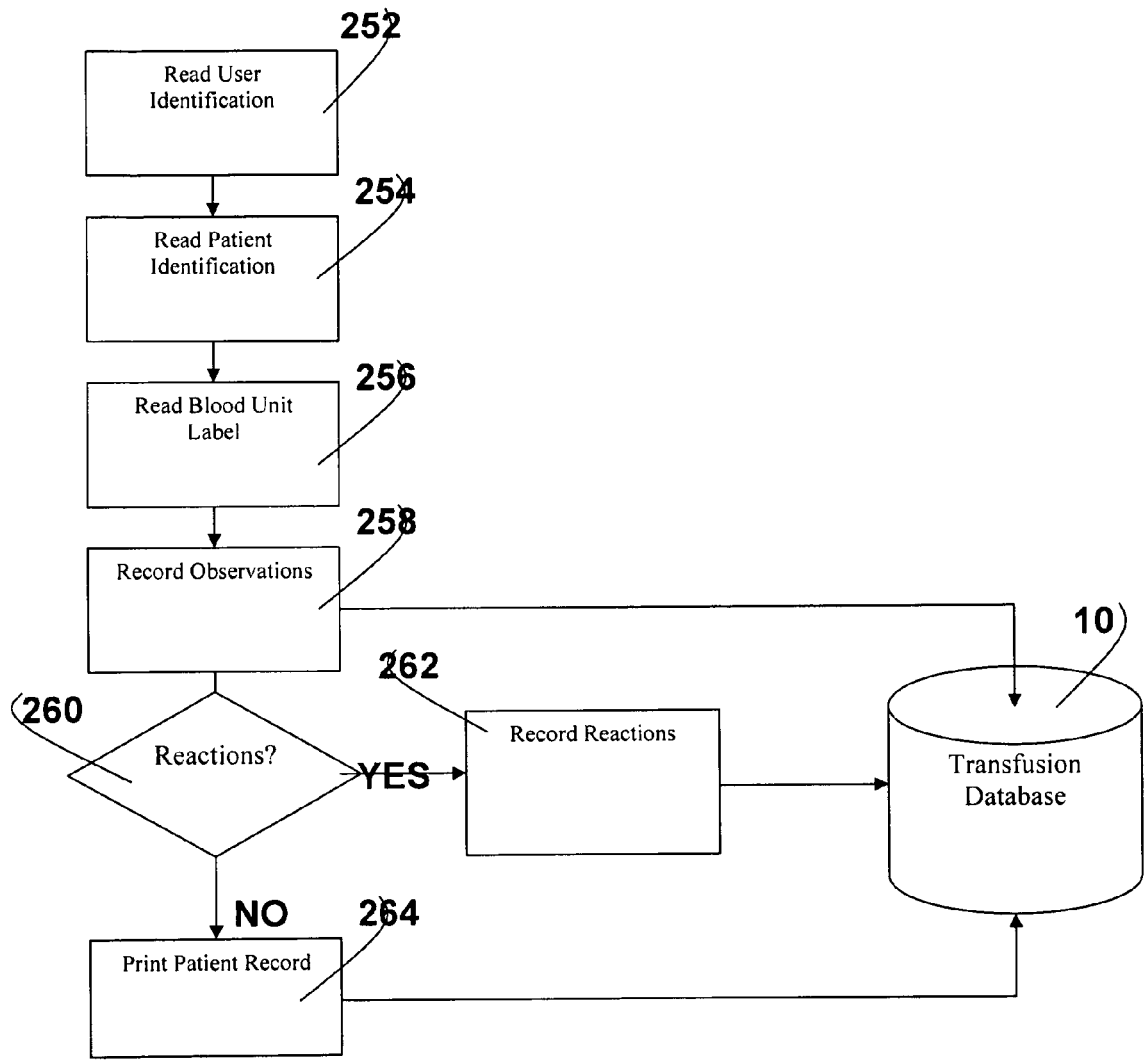

FIG. 8B illustrates the procedure for recording the patient's vital signs or any transfusion reactions that may occur while transfusing blood into a patient, using the apparatus depicted in FIG. 2. Accepted practice dictates that a patient's vital signs be recorded every 15 minutes or so during a transfusion. It is also expected that any reactions to the blood transfusion will be promptly recorded.

The software on PDA 118 includes means for recording the patient's vital signs and any reactions that might be noticed. In the first step of the recording process, PDA 118 displays a message asking the caregiver to read their caregiver code 112 (step 240). To do this, the caregiver uses reader 120 of PDA 118 and either scans caregiver code 112 (if caregiver code 112 is a barcode) or brings reader 120 within range of caregiver code 112 (if caregiver code 112 is an RFID tag). PDA 118 displays caregiver code 112 so that the caregiver can verify it.

Next, PDA 118 displays a message requesting the caregiver to read patient code 116 (step 242). Using reader 120 of PDA 118, the caregiver either scans patient code 116 (if patient code 116 is a barcode) or brings reader 120 within range of patient code 116 (if patient code 116 is an RFID tag). PDA 118 displays the patient identification information encoded in patient code 116. In the exemplary embodiment presented herein, this display includes the patient's identification number, surname, forename, date of birth and sex. PDA 118 displays a message asking the caregiver to confirm that the patient information is correct. Caregivers are expected to ask the patient their name and date of birth to ensure that the displayed information is correct before proceeding with the observation.

If the caregiver is satisfied that the information read from wristband 114 is correct, they press a button on PDA 118 to confirm that they have checked the information. PDA 118 then displays a message requesting the caregiver to read the blood unit identification from the blood unit currently being transfused. This ensures that any observations or reactions are associated with the correct blood unit. The caregiver uses reader 120 of PDA 118 and either scans the blood unit label (if the blood unit label includes a barcode) or brings reader 120 within range of the blood unit label (if the blood unit label includes an RFID tag). PDA 118 displays the blood unit identification so that the caregiver can verify it.

If the caregiver is satisfied that the information read from the blood unit label is correct, they press a button on PDA 118 to confirm that they have checked the information PDA 118 now provides a screen on which the caregiver may enter the patient's vital signs (step 244).

As soon as the vital signs are entered, PDA 118 transmits a record to transfusion database 10, recording the vital signs observations. In the exemplary embodiment presented herein, PDA 118 uses s a wireless network connection to insert the observation record into transfusion database 10. The observation record includes the observations recorded, the patient identification information read from patient code 116, the blood unit information read from the blood unit label, caregiver code 112, the time and date and a unique identifier for PDA 118.

Once the vital signs are entered, a message on PDA 118 asks the caregiver to press a button if any reactions are noted. If the button is pressed (step 246), PDA 118 offers a list of common reactions from which the caregiver may choose, or a place into which the caregiver can enter specific notes about reactions (step 248).

As soon as any reactions are noted, PDA 118 transmits a record to transfusion database 10, recording the reactions. In the exemplary embodiment presented herein, PDA 118 uses s a wireless network connection to insert the reactions record into transfusion database 10. The reactions record includes the reactions recorded, the patient identification information read from patient code 116, the blood unit information read from the blood unit label, caregiver code 112, the time and date and a unique identifier for PDA 118.

At this stage, PDA 118 also displays a button for printing. The caregiver connects PDA 118 to printer 124 and presses the print button, which causes printer 124 to produce patient observation label 122 (step 250). Patient observation label 122 shows the patient's vital signs, patient identification, caregiver code 112, the blood unit number, the time and date and any reactions that were observed. Patient observation label 122 may also include a barcode encoding some or all of this information. In the exemplary embodiment presented herein, the printed patient record includes a PDF-417 two-dimensional barcode which encodes the patient identification information read from patient code 116, the blood unit information read from the blood unit label, caregiver code 112, the time and date, the patient's vital signs and any reactions noted, and a unique identifier for PDA 118.

In an alternative embodiment, PDA 118 is not equipped with a wireless network connection, or there is no wireless network available at the location where the observation is made. In this case, the software on PDA 118 causes a second copy of patient record label 122 to be printed by printer 124. This second label, which in this embodiment includes a PDF-417 two-dimensional barcode as described above, is taken to a computer connected to transfusion database 10. This computer is equipped with a barcode reader capable of reading the PDF-417 barcode and inserting the information read into transfusion database 10.

Figure illustrates the procedure for recording the end of the transfusion process using the apparatus of FIG. 2.

In the first step of recording the end of a transfusion, PDA 118 displays a message asking the caregiver to read their caregiver code 112 (step 252). To do this, the caregiver uses reader 120 of PDA 118 and either scans caregiver code 112 (if caregiver code 112 is a barcode) or brings reader 120 within range of caregiver code 112 (if caregiver code 112 is an RFID tag). PDA 118 displays caregiver code 112 so that the caregiver can verify it.

Next, PDA 118 displays a message requesting the caregiver to read patient code 116 (step 254). Using reader 120 of PDA 118, the caregiver either scans patient code 116 (if patient code 116 is a barcode) or brings reader 120 within range of patient code 116 (if patient code 116 is an RFID tag). PDA 118 displays the patient identification information encoded in patient code 116. In the exemplary embodiment presented herein, this display includes the patient's identification number, surname, forename, date of birth and sex. PDA 118 displays a message asking the caregiver to confirm that the patient information is correct. Caregivers are expected to ask the patient their name and date of birth to ensure that the displayed information is correct before proceeding with the end transfusion record.

If the caregiver is satisfied that the information read from wristband 114 is correct, they press a button on PDA 118 to confirm that they have checked the information. PDA 118 then displays a message requesting the caregiver to read the blood unit identification from the blood unit currently being transfused (step 256). This ensures that the end transfusion record and any observations or reactions are associated with the correct blood unit. The caregiver uses reader 120 of PDA 118 and either scans the blood unit label (if the blood unit label includes a barcode) or brings reader 120 within range of the blood unit label (if the blood unit label includes an RFID tag). PDA 118 displays the blood unit identification so that the caregiver can verify it.

If the caregiver is satisfied that the information read from the blood unit label is correct, they press a button on PDA 118 to confirm that they have checked the information PDA 118 now provides a screen on which the caregiver may enter the patient's vital signs (step 258).

As soon as the vital signs are entered, PDA 118 transmits a record to transfusion database 10, recording the vital signs observations. In the exemplary embodiment presented herein, PDA 118 uses a wireless network connection to insert the observation record into transfusion database 10. The observation record includes the observations recorded, the patient identification information read from patient code 116, the blood unit information read from the blood unit label, caregiver code 112, the time and date and a unique identifier for PDA 118.

Once the vital signs are entered, a message on PDA 118 asks the caregiver to press a button if any reactions are noted. If the button is pressed (step 260), PDA 118 offers a list of common reactions from which the caregiver may choose, or a place into which the caregiver can enter specific notes about reactions (step 262).

As soon as any reactions are noted, PDA 118 transmits a record to transfusion database 10, recording the reactions. In the exemplary embodiment presented herein, PDA 118 uses a wireless network connection to insert the reactions record into transfusion database 10. The reactions record includes the reactions recorded, the patient identification information read from patient code 116, the blood unit information read from the blood unit label, caregiver code 112, the time and date and a unique identifier for PDA 118.

Whether or not reactions are noted, PDA 118 transmits a record to transfusion database 10, recording the completion of the transfusion. In the exemplary embodiment presented herein, PDA 118 uses a wireless network connection to insert the end transfusion record into transfusion database 10. The end transfusion record includes a code to indicate that the transfusion is complete, the patient identification information read from patient code 116, the blood unit information read from the blood unit label, caregiver code 112, the time and date and a unique identifier for PDA 118.

At this stage, PDA 118 also displays a button for printing. The caregiver connects PDA 118 to printer 124 and presses the print button, which causes printer 124 to produce end transfusion label 122 (step 264). End transfusion label 122 shows the patient's vital signs, patient identification, caregiver code 112, the blood unit number, the time and date any reactions that were observed and an indication that the transfusion is complete. Patient observation label 122 may also include a barcode encoding some or all of this information. In the exemplary embodiment presented herein, the printed patient record includes a PDF-417 two-dimensional barcode which encodes the patient identification information read from patient code 116, the blood unit information read from the blood unit label, caregiver code 112, the time and date, the patient's vital signs and any reactions noted, and a unique identifier for PDA 118.

In an alternative embodiment, PDA 118 is not equipped with a wireless network connection, or there is no wireless network available at the location where the observation is made. In this case, the software on PDA 118 causes a second copy of patient record label 122 to be printed by printer 124. This second label, which in this embodiment includes a PDF-417 two-dimensional barcode as described above, is taken to a computer connected to transfusion database 10. This computer is equipped with a barcode reader capable of reading the PDF-417 barcode and inserting the information read into transfusion database 10.

Figure 9:
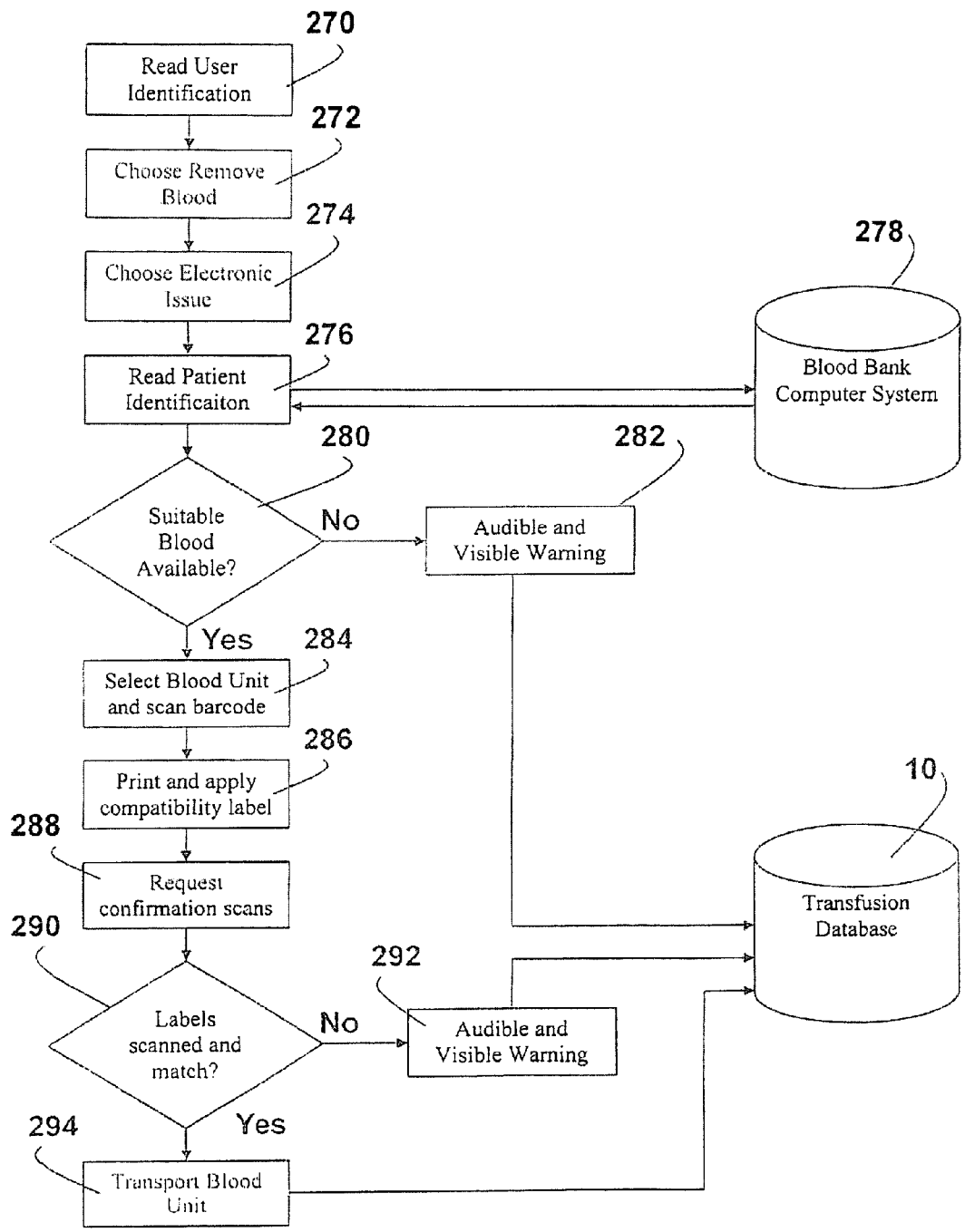
FIG. 9 is a flowchart for the remote electronic issue of blood using the apparatus of FIG. 6.
Figure 1:
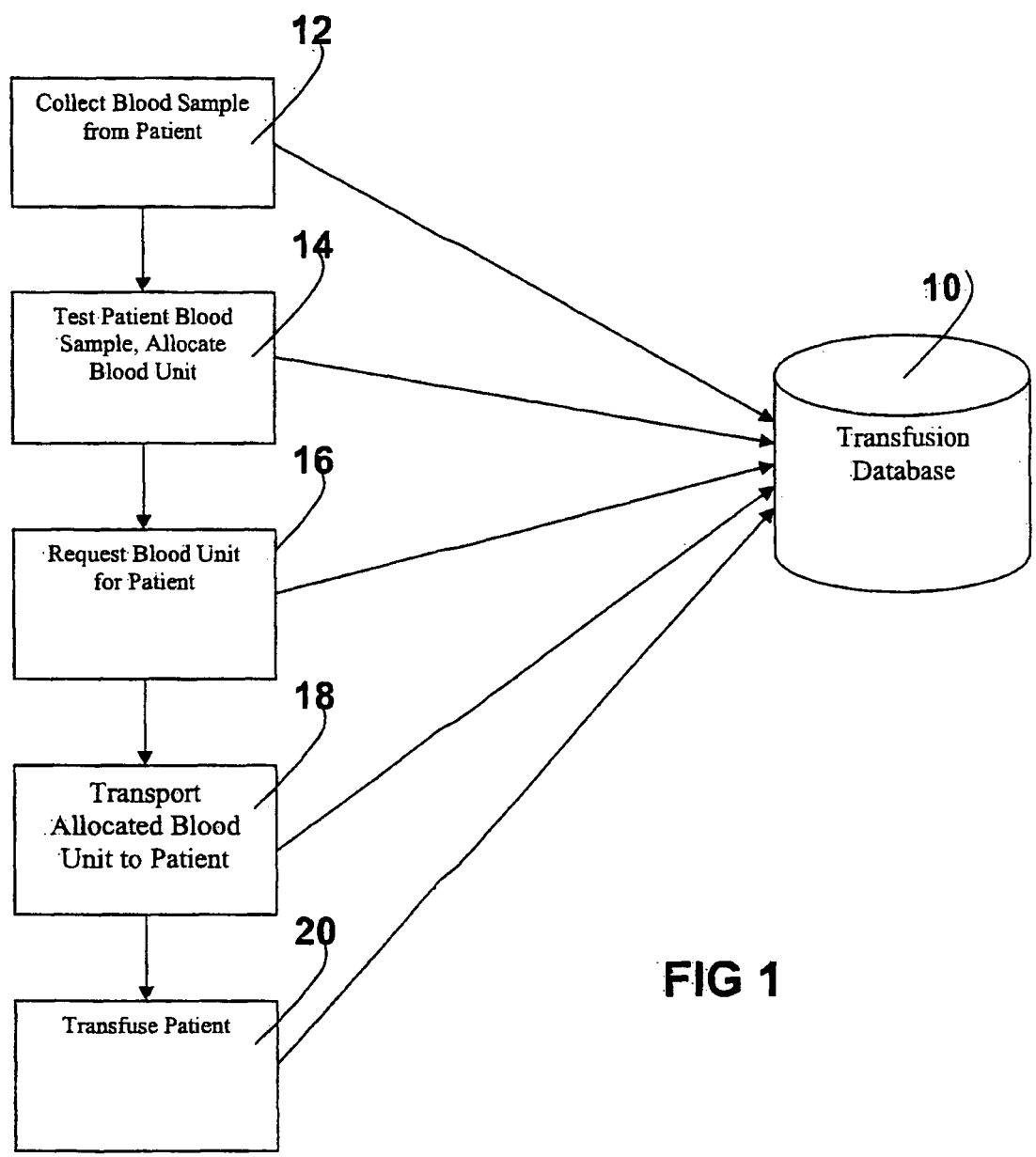
Figure 2:
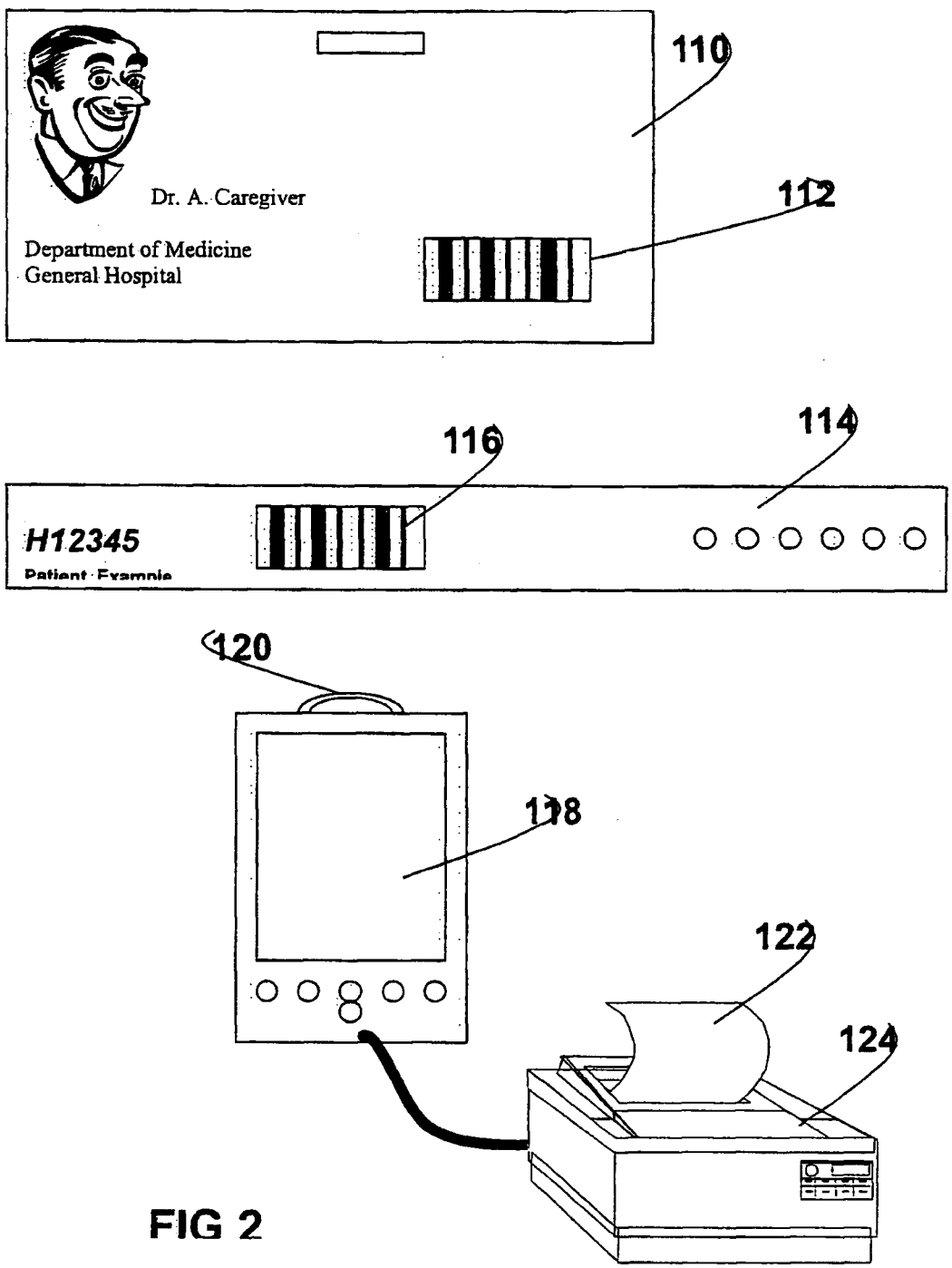
Figure 3:
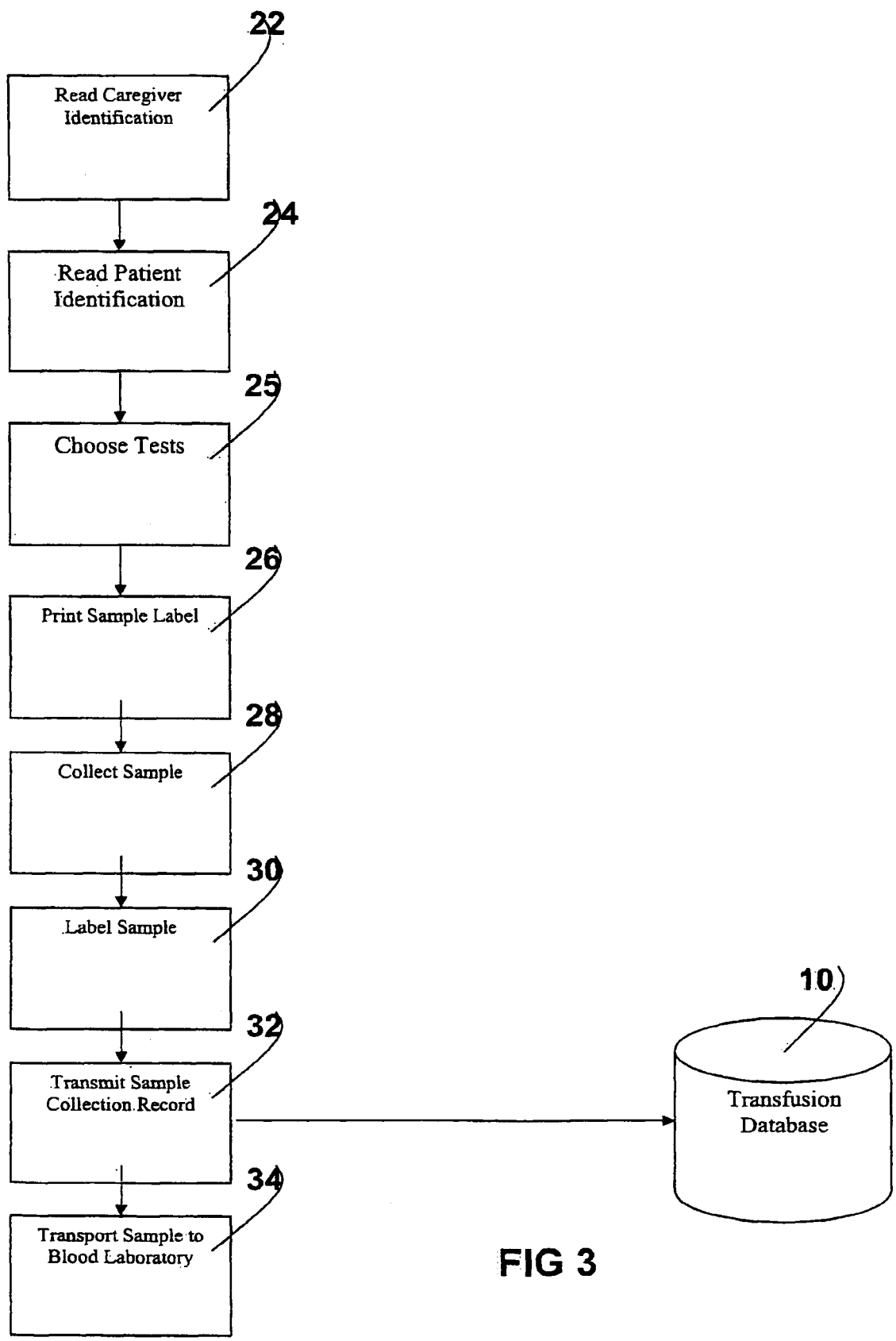
Figure 4:
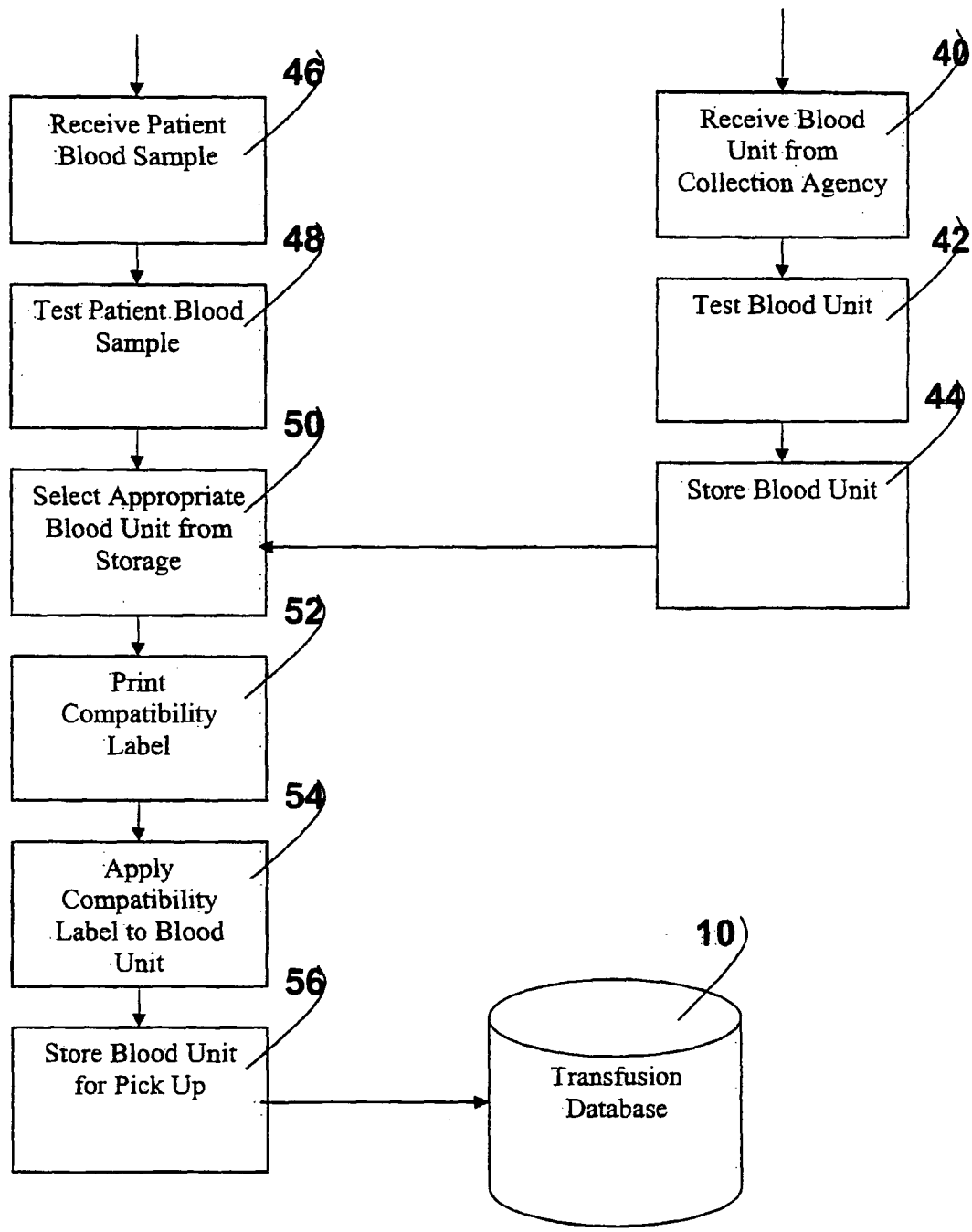

FIG. 9 illustrates a means for improving the safety and efficiency of electronic issue of blood using the apparatus of FIG. 6.

In this embodiment of the invention, the caregiver collecting a blood unit identifies themselves by scanning the caregiver code 112 on their caregiver identification 110, using reader 64, which in this embodiment is a barcode reader (step 270). Software located on computer 66 determines if the caregiver identified by caregiver code 112 is authorized to collect blood units, and if so, displays two buttons on touch screen 62. The caregiver touches the appropriate button to indicate that they intend to remove blood from the refrigerator (step 272). This causes the display of touch screen 62 to offer the choice of removing a pre-allocated blood unit, or using electronic issue. The caregiver touches the electronic issue button on touch screen 62 (step 274).

The software on computer 66 now uses speaker 74 and the display of touch screen 62 to ask the caregiver read the request slip printed when blood was requested for the patient (FIG. 1 step 16). The caregiver uses reader 64 to read the two-dimensional barcode on the request slip (step 276). The software on computer 66 sends a message to blood bank computer system 278 asking if the patient identified by the caregiver is suitable for electronic issue. Blood bank computer system 278 returns a message indicating if the patient is eligible for electronic issue, and if so, what type of blood should be issued.

The software on computer 66 now determines if suitable blood for the identified patient is available. It does this by checking to see if a suitable blood unit is recorded as having been placed in the current storage location (step 280). If no suitable blood is available, the software on computer 66 uses speaker 74 and the display of touch screen 62 to tell the caregiver that no blood is available (step 282) and records the attempted transaction in transfusion database 10. If suitable blood is available, the software on computer 66 uses speaker 74 and the display of touch screen 62 to tell the caregiver to select an appropriate blood unit from refrigerator 70.

The software on computer 66 now unlocks lock 68 on refrigerator 70. In an alternative embodiment, refrigerator 70 is a multi-compartment refrigerator, wherein each compartment has a separate lock 68. In this embodiment, only the compartment of refrigerator 70 which contains blood of the right type for the patient identified is unlocked, thereby preventing access to blood of the wrong type for the patient.

The software on computer 66 uses speaker 74 and the display of touch screen 62 to ask the caregiver to select the blood unit they wish to remove, and to scan a barcode on the blood unit that uniquely identifies the blood unit (step 284). The software on computer 66 then causes compatibility label 71 to be printed on printer 73. Now the software on computer 66 uses speaker 74 and the display of touch screen 62 to ask the caregiver to apply compatibility label 71 to the blood unit (step 286), then scan both the barcode on the blood unit that unique identifies the blood unit and compatibility label 71 (step 288).

If the barcode on the blood unit and the information in compatibility label 71 match, and if both barcodes were scanned within a short period (five seconds in the exemplary embodiment presented herein), the software on computer 66 uses the display of touch screen 62 to tell the caregiver that the blood unit is safe to transport (step 294). If the information fails to match, the software on computer 66 uses speaker 74 and the display of touch screen 62 to tell the caregiver that the blood is incorrectly labelled and should not be used (step 292). In either case, a record of the transaction is stored in transfusion database 10.

Should the two barcodes not be scanned within the allowed time period, the software on computer 66 uses the display of touch screen 62 to tell the caregiver to try scanning the labels again. The short time delay between the two scans ensures that label 71 is attached to the blood unit and that label 71 and the blood unit are not being scanned separately.

From the detailed description above, it can be seen that the invention provides means for recording every step in the transfusion process, including all movements of the blood unit prior to transfusion. Each of the steps is recorded in transfusion database 10. It will be obvious to one skilled in the art that data collected in this way can easily be read into a database program such as Microsoft Access (Microsoft Corporation, www.microsoft.com) from which various reports can be created. It is also possible, with the same database program, to determine the complete history of any particular blood unit or blood units.

Furthermore, the exemplary embodiment presented herein of the invention (in which PDA 118 is wirelessly connected to transfusion database 10) provides a means for monitoring blood transfusion as they occur. As every step in the transfusion process is immediately recorded in transfusion database 10, it is a simple matter to determine which blood units are currently being transfused at any time.

Many different adaptations and variations of the subject invention are possible without departing from the scope and spirit of the present invention, therefore, the present invention should be limited only by the scope of the appended claims. For example the delivery of drugs to patients presents many of the same problems as those described herein for blood transfusion. It would be clear to one skilled in the art that a system similar to that described here could be used to control the collection and administration of drugs to a patient.

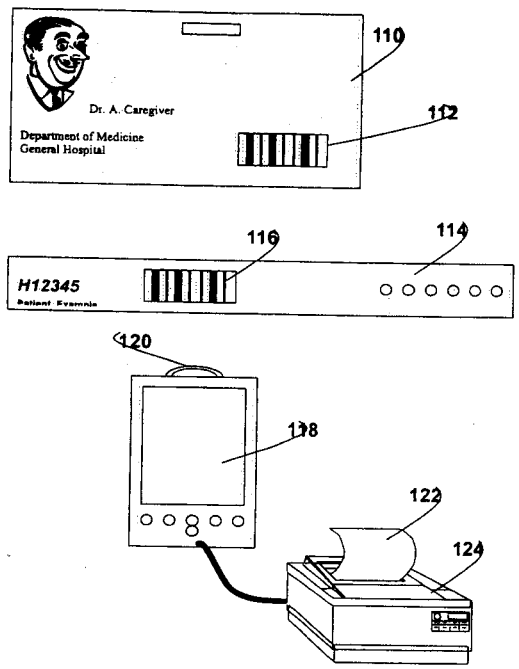

The invention claimed is:

1. An apparatus for implementing blood sample collection, blood unit requesting, and blood unit transfusion into a patient, said apparatus comprising:
a caregiver identity means comprising an electronically readable caregiver code;
a patient identification wristband comprising an electronically readable patient code;
a portable computer comprising a reader wherein said reader is capable of reading said caregiver code and said patient code and software to implement the process of sample collection wherein said process of sample collection comprises the step of causing said portable computer to present messages to a caregiver that indicate to said caregiver a predefined series of steps, presented step-by-step, to be performed by said caregiver in the sample collection process and
a portable printer wherein said portable printer is capable of communicating with said portable computer.

2. The apparatus of claim 1 wherein said caregiver identity means is an employee identification card and wherein said employee identification card comprises said caregiver code.

3. The apparatus of claim 1 wherein said electronically readable caregiver code includes multiple categories of data and is selected from the group consisting of a two-dimensional barcode, and a Radio Frequency Identification (RFID) tag.

4. The apparatus of claim 1 wherein said electronically readable patient code includes multiple categories of data and is selected from the group consisting of a two-dimensional barcode, and a Radio Frequency Identification (RFID) tag.

5. The apparatus of claim 4 wherein said two-dimensional barcode is selected from the group consisting of PDF 417, Aztec code, and Matrix code.

6. The apparatus of claim 1 wherein said portable computer is a Personal Digital Assistant (PDA) and wherein said reader is selected from the group consisting of a barcode scanner, a barcode imager, and an RFID reader.

7. The apparatus of claim 6 wherein said PDA comprises a wireless network means for communicating with a wireless network, a touch screen, and a communication means for communicating with said portable printer.

8. The apparatus of claim 1 wherein said messages to the caregiver comprise the following:
a request to said caregiver to read a caregiver code;
a request to said caregiver to read a patient code;
a request to said caregiver to verify the accuracy of displayed patient identification information;
a selection of tests for said caregiver to request for a blood sample; and a request to said caregiver to print a blood sample label.

9. The apparatus of claim 8 wherein said selection of tests are automatically assigned by said portable computer.

10. The apparatus of claim 9 wherein said portable computer further comprises a timer wherein said timer prevents said caregiver from printing said blood sample label if more than a pre-set time has passed since said patient code was read.

11. The apparatus of claim 9 further comprising a request to said caregiver to verify that said blood sample collection is complete, wherein the caregiver enters verification data in said portable computer.

12. The apparatus of claim 9 wherein said portable computer transmits a record to a transfusion database.

13. The apparatus of claim 12 wherein said information is transmitted to said transfusion database via a wireless network connection.

14. The apparatus of claim 13 wherein a barcode reader connected to a computer connected to said transfusion database is capable of scanning said sample collection label and writing said blood sample request information into said transfusion database.

15. An apparatus for implementing blood sample collection, blood unit requesting, and blood unit transfusion into a patient, said apparatus comprising:
a caregiver identity means comprising an electronically readable caregiver code;
a patient identification wristband comprising an electronically readable patient code;
a portable computer comprising a reader wherein said reader is capable of reading said caregiver code and said patient code and software to implement the process of sample collection wherein said process of sample collection comprises the step of causing said portable computer to display messages to a caregiver that indicate to said caregiver the next step in a predefined series of steps to be performed by said caregiver;
a portable printer wherein said portable printer is capable of communicating with said portable computer; and
a lockable refrigerated storage compartment for storing a blood unit, including a computer and software installed on said computer, said software in combination with said computer capable of instructing said lockable refrigerator to become locked or to become unlocked.

16. The apparatus of according to claim 15 including recording means for recording the movement of a blood unit into and out of said refrigerated storage compartment, said recording means comprising:
a first Radio Frequency Identification (RFID) tag attached to a blood unit, wherein said RFID tag encodes a blood unit identification code for said blood unit;
a second RFID tag for a user of said apparatus, wherein said second RFID tag encodes a user identification code;
an antenna disposed to read all RFID tags inside and in the vicinity of a refrigerated storage compartment;
a device for receiving data via said antenna from said first RFID tag and said second RFID tag and sending said received data to a computer; and
a computer for receiving data from said data receiving device.

17. An apparatus for implementing blood sample collection, blood unit requesting, and blood unit transfusion into a patient, said apparatus comprising:

an electronically readable caregiver code; an electronically readable patient wristband with an electronically readable patient code;

a first computer including an electronic reader, wherein said reader is capable of reading said caregiver code and said patient code;

software to implement to process of sample collection wherein said process of sample collection comprises the step of causing said first computer to display messages to a caregiver that indicate to said caregiver the next step in a predefined series of steps to be performed by said caregiver;

a portable printer capable of communicating with said first computer; and a lockable refrigerated storage compartment for storing a blood unit, including a second computer and software installed on said second computer, said software in combination with said second computer capable of instructing said lockable refrigerator to become locked or to become unlocked.

18. The apparatus according to claim 17 including:

a reader connected to said second computer;

a speaker connected to said second computer; and a touch screen, wherein said touch screen provides a visual display and a touch operated user interface for operating said software installed on said second computer.

19. The apparatus of claim 18 wherein said software installed on said second computer determines if the caregiver identified by said caregiver code is authorized to collect blood units and wherein when said caregiver is authorized to collect blood units, two buttons are displayed on said touch screen wherein a first of said two buttons indicates that caregiver is adding a blood product to said refrigerated storage compartment and wherein a second of said two buttons indicates that a caregiver is removing a blood product from said refrigerated storage compartment.

20. An apparatus for implementing blood sample collection, blood unit requesting, and blood unit transfusion into a patient, said apparatus comprising:

an electronically readable caregiver code;

an electronically readable patient wristband with an electronically readable patient code;

a first computer including an electronic reader, said reader capable of reading said caregiver code and said patient code;

software to implement to process of sample collection wherein said process of sample collection includes the step of causing said first computer to display messages to a caregiver that indicate to said caregiver the next step in a predefined series of steps to be performed by said caregiver;

a printer capable of communicating with said first computer;

recording means for recording the movement of a blood unit into and out of a refrigerated storage compartment, said recording means comprising a first Radio Frequency Identification (RFID) tag attached to a blood unit, wherein said RFID tag encodes a blood unit identification code for said blood unit, a second RFID tag for a user of said apparatus, wherein said second RFID tag encodes a user identification code;

an antenna disposed to read all RFID tags inside and in the vicinity of the refrigerated storage compartment;

a device for receiving data via said antenna from said first RFID tag and said second RFID tag and sending said received data to a computer; and a second computer for receiving data from said data receiving device.

* * * * *

UNITED STATES PATENT AND TRADEMARK OFFICE
CERTIFICATE OF CORRECTION

PATENT NO.        : 8,261,981 B2  
APPLICATION NO.   : 12/354120  
DATED             : September 11, 2012  
INVENTOR(S)       : Auchinleck Page 1 of 7

It is certified that error appears in the above-identified patent and that said Letters Patent is hereby corrected as shown below:

Title page should be deleted and substitute therefor the attached title page as shown on the attached page.

Replace figures 1-5 with the attached figures 1-5

Signed and Sealed this  
Twelfth Day of February, 2013

Teresa Stanek Rea  
*Acting Director of the United States Patent and Trademark Office*

(12) United States Patent
Auchinleck

(10) Patent No.: US 8,261,981 B2
(45) Date of Patent: Sep. 11, 2012

(54) APPARATUS AND METHODS FOR MONITORING TRANSFUSION OF BLOOD

(75) Inventor: Geoffrey Fletcher Auchinleck, Vancouver (CA)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 12/354,120

(22) Filed: Jan. 15, 2009

(65) Prior Publication Data
US 2009/0121009 A1 May 14, 2009

Related U.S. Application Data

(63) Continuation of application No. 11/061,899, filed on Feb. 18, 2005, now Pat. No. 7,490,766, which is a continuation-in-part of application No. 10/783,438, filed on Feb. 19, 2004, now Pat. No. 6,983,884.

(51) Int. Cl.
*G07B 15/02* (2011.01)

(52) U.S. Cl. ............ 235/384; 235/385; 235/462.07; 700/86; 700/242; 705/2; 238/117; 604/67

(58) Field of Classification Search ............ 235/384, 235/385, 462.07; 700/86, 242; 705/2; 238/117; 604/67
See application file for complete search history.

(56) References Cited

U.S. PATENT DOCUMENTS

| | | | |
|---|---|---|---|
| 4,953,745 A | 9/1990 | Rowlett, Jr. | |
| 5,193,855 A * | 3/1993 | Shamos | 283/117 |
| 5,790,409 A | 8/1998 | Fedor et al. | |
| 5,912,818 A | 6/1999 | McGrady et al. | |
| 6,260,761 B1 * | 7/2001 | Peoples, Jr. | 235/462.07 |
| 7,349,858 B1 | 3/2008 | McGrady et al. | |
| 2002/0068358 A1 * | 6/2002 | Campbell et al. | 435/289.1 |
| 2004/0186376 A1 * | 9/2004 | Hogg et al. | 600/424 |
| 2005/0119914 A1 * | 6/2005 | Batch | 705/2 |
| 2008/0103437 A1 * | 5/2008 | Duchon et al. | 604/67 |
| 2009/0204508 A1 * | 8/2009 | Podgurny et al. | 705/26 |

* cited by examiner

*Primary Examiner* — Allyson Trail

(57) ABSTRACT

Apparatus and methods are described for ensuring that blood transfused into a patient is the correct blood for that patient, is transfused in the correct manner and that a complete audit trail is created that will allow later tracing of blood from donation through to ultimate transfusion.

20 Claims, 13 Drawing Sheets